United States Patent
Bassett et al.

(10) Patent No.: US 11,767,402 B2
(45) Date of Patent: Sep. 26, 2023

(54) METHODS OF FORMING IONICALLY CROSS-LINKED GELS

(71) Applicant: Nordovo Biosciences AS, Oslo (NO)

(72) Inventors: David Charles Bassett, Birmingham (GB); Armend Gazmeno Håti, Oslo (NO)

(73) Assignee: Nordovo Biosciences AS, Oslo (NO)

( * ) Notice: Subject to any disclaimer, the term of this patent is extended or adjusted under 35 U.S.C. 154(b) by 110 days.

(21) Appl. No.: 17/214,700

(22) Filed: Mar. 26, 2021

(65) Prior Publication Data

US 2021/0317274 A1 Oct. 14, 2021

Related U.S. Application Data

(63) Continuation of application No. 16/083,370, filed as application No. PCT/IB2017/051394 on Mar. 9, 2017, now Pat. No. 10,988,583.

(30) Foreign Application Priority Data

Mar. 9, 2016 (GB) ..................................... 1604076

(51) Int. Cl.
| | |
|---|---|
| *C08J 3/075* | (2006.01) |
| *C08J 3/24* | (2006.01) |
| *C08L 5/04* | (2006.01) |
| *C08L 5/06* | (2006.01) |
| *C08K 3/08* | (2006.01) |
| *C08K 5/17* | (2006.01) |
| *A61L 15/60* | (2006.01) |
| *A61L 27/52* | (2006.01) |
| *C08L 89/06* | (2006.01) |
| *C08B 37/00* | (2006.01) |
| *C08H 1/06* | (2006.01) |

(52) U.S. Cl.
CPC ............... *C08J 3/075* (2013.01); *A61L 15/60* (2013.01); *A61L 27/52* (2013.01); *C08B 37/0084* (2013.01); *C08H 1/06* (2013.01); *C08J 3/241* (2013.01); *C08K 3/08* (2013.01); *C08K 5/175* (2013.01); *C08L 5/04* (2013.01); *C08L 5/06* (2013.01); *C08L 89/06* (2013.01); *C08J 2305/04* (2013.01); *C08J 2305/06* (2013.01); *C08K 2003/0856* (2013.01); *C08K 2003/0893* (2013.01)

(58) Field of Classification Search
CPC .................................. C08J 3/075; C08J 3/241
See application file for complete search history.

(56) References Cited

U.S. PATENT DOCUMENTS

| | | | | |
|---|---|---|---|---|
| 2011/0117172 | A1* | 5/2011 | Gopferich | ............... A61P 27/02 424/428 |
| 2012/0270209 | A1 | 10/2012 | Shah et al. | |

OTHER PUBLICATIONS

Chen and Peng, Advances in Environmental Research, 3 (4) 2000, 439-449.*
Andersen et al., Microarrays 2015, 4, 133-161.*
(Continued)

*Primary Examiner* — Vu A Nguyen
(74) *Attorney, Agent, or Firm* — Honigman LLP; Fernando Alberdi; Jonathan P. O'Brien

(57) ABSTRACT

The present invention relates to the formation of gels. In particular, the present invention is directed to a method of forming a cross-linked polymer hydrogel using competitive ligand exchange.

21 Claims, 12 Drawing Sheets

(56) References Cited

OTHER PUBLICATIONS

Figure 1:
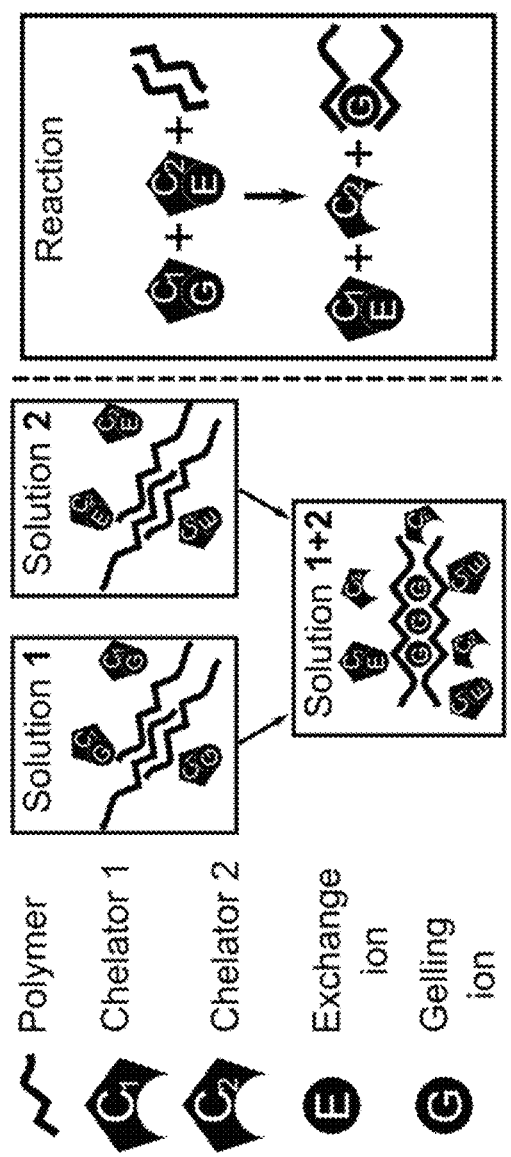

Potter et al., Magnetic Resonance Imaging, vol. 12, No. 2, pp. 309-311, 1994.*
Stokke et al., Macromolecules 2000, 33, 1853-1863.*
Anderson et al., "3D Cell Culture in Alginate Hydrogels", Microarrays, 4(2):133-161, 2015.
Chen et al., "Uptake of Toxic Metal Ions by Novel Calcium Alginate Beads", Advances in Environmental Research, 3 (4):439-444, 2000.
Hati, A. et al., ""Versatile, cell and chip friendly method to gel alginate in microfluidic devices,"" Lab Chip, 2016, 16 (19), 3617-3846.
Huynh et al., "Binding of Divalent Cations to Polygalacturonate: A Mechanism Driven by the Hydration Water", The Journal of Physical Chemistry Part B, 120(5): 1021-1032, 2016.

PCT International Search Report, PCT/IB2017/051394, dated Jul. 3, 2017 (5 pages).
Potter et al., "Magnetic Resonance Imaging (MRI) of Calcium Alginate Gels", Magnetic Resonance Imaging, 12 (2):309-311, 1994.
Schmidt et al., "Hydrogels used for cell-based drug delivery", Journal of Biomedical materials Research, Part A, 87A (4):1113-1122, 2008.
Stokke et al., "Small-Angle X-ray Scattering and Rheological Characterization of Alginate Gels 1. Ca-Alginate Gels", Macromolecules, 33(5): 1853-18653, 2000.
Straccia et al., "Alginate Hydrogels Coated with Chitosan for Wound Dressing", Marine Drugs, 13(5):2890-2908, 2015.
Wang, Q. et al., ""Alginate droplets pre-crosslinked in microchannels to preparemonodispersed spherical microgelsQin Wang, Shanshan Liu, Hong Wang, Jintao Zhu,"" Colloids and Surfaces A: Physicochem. Eng. Aspects, 2015, 482, 371-377.

* cited by examiner

METHODS OF FORMING IONICALLY CROSS-LINKED GELS

CROSS-REFERENCE TO RELATED APPLICATIONS

This application is a continuation application that claims the benefit of, and claims priority to U.S. patent application Ser. No. 16/083,370, filed Sep. 7, 2018, which claims priority to PCT International Application No. PCT/IB2017/051394, filed Mar. 9, 2017, which claims the benefit of Great Britain Application Serial No. 1604076.8, filed Mar. 9, 2016, the entire contents of both disclosures are incorporated herein by reference in their entireties.

FIELD OF INVENTION

The present invention relates to improvements relating to the formation of gels. In particular, the present invention is directed to an improved method of forming a cross-linked polymer hydrogel using competitive ligand exchange. In another aspect of the invention there is provided an improved cross-linked polymeric gel obtained by the method of the present invention. In a further aspect of the invention there is provided a kit of parts for making the cross-linked polymer gels of the present invention. In an even further aspect of the invention there are provided a variety of uses for the gels of the present invention.

BACKGROUND OF INVENTION

Hydrogel forming polymers may be of natural or synthetic origin. Hydrogels are used in a very wide range of applications within food, pharmaceutical and biomedical industries amongst others. This class of materials are composed of a three dimensional polymer network stabilised in an aqueous phase by physical and/or chemical cross-links. Chemically cross-linked hydrogels contain permanent junctions formed by covalent bonds (e.g. polyacrylamide, polyethylene glycol (PEG), hyaluronic acid, chitosan derivatives etc.), while physical networks have transient, reversible junctions derived from polymer chain entanglements (e.g. polyvinyl alcohol, collagen, gelatin, many polysaccharides), ionic (e.g. alginate, pectin etc.) and hydrogen bonding or hydrophobic interactions. Hydrogels can also be formed following modification of water soluble polymers to incorporate reactive groups into the polymer chain, rendering the polymer cross-linkable by chemical means, or reactive to stimuli such as light, heat or pH or combinations thereof.

Chemical cross-linking may offer good control of the gel formation kinetics and degree of cross-linking. However, chemical modification of polymers has several drawbacks, particularly for biomedical, pharmaceutical and food applications, where the chemical purity and reactivity may hinder the materials performance in a given application, such as rendering a material inflammatory, non-biocompatible or toxic. Therefore regulatory issues may arise. In addition, such modification adds complexity and associated expenses to the final product.

For biomedical applications, ionic cross-linking is especially attractive since it does not require covalent modification of the polymer and offers a mild and reversible route to gel formation which is attractive for applications such as protein structure preservation and cell encapsulation. However, the kinetics of ionically cross-linked gel processes are difficult to control as they are governed by the interactions between the ionotropic polymer and inorganic ions. Typically, ionic gelling occurs extremely rapidly, limited by ionic diffusion which in water is very fast (e.g. $Ca^{2+}$ diffusion coefficient in water$\approx 1.2\times 10^{-5}$ $cm^2$ $s^{-1}$). This means that applications requiring on demand gelation (such as therapeutic compositions that are required to be injectable at the point of administration) are difficult or not feasible using this approach.

Slower, acid dependent gelling mechanisms, so called internal gelation methods, have also been extensively studied. These rely on the gelling ion being contained within the polymer solution either as a chelate, typically Ca-Ethylenediaminetetraacetic acid (Ca-EDTA), K. Toft, Progress in Food and Nutrition Science 1982, 6, 89, or as a solid, typically calcium carbonate ($CaCO_3$), K. I. Draget, K. Ostgaard, O. Smidsrød, Applied Microbiology and Biotechnology 1989, 31, 79. WO2006044342 and US20110117172 both disclose prior art methods requiring pH changes to release calcium ions, leading to cross-linking of the polymer. $Ca^{2+}$ may be generated by either lowering the pH rapidly by the introduction of an aqueous acid or more slowly by the hydrolysis of D-glucono-b-lactone (GDL) allowing for a slow formation of the gel allowing injectable or mouldable preparations to be achieved. However, when Ca-EDTA complexes are used, the pH must be reduced below pH5 to release $Ca^{2+}$ ions which may be prohibitive for certain applications such as cell or protein encapsulation. Modifying the amounts of $CaCO_3$/GDL may allow gelling to occur at neutral conditions, reducing problems associated with low pH. However, $CO_2$ gas is generated which causes bubbles in gels. Additionally, use of a solid source of calcium causes restrictions for small scale gel production, particularly in microfluidic droplet generation where solid $CaCO_3$ may clog microchannels. The use of a solid $CaCO_3$ source also means that the preparation cannot be sterilised by filtration and there may also be problems with sedimentation of the solid particles resulting in inhomogeneous distribution of calcium within the gel. With regards to the GDL component, the hydrolysis of this chemical is extremely slow, and gels produced by this method take several hours to fully cross-link. Although there is some control over gelling kinetics by changing the particle size of $CaCO_3$, gelling is always in the timescale of hours. Also, a GDL solution must be freshly prepared since it naturally begins hydrolysing on contact with water. Despite many years of research, no simple and versatile method to control the kinetics of ionotropic gel formation exist.

It would therefore be beneficial to provide an improved process for the production of gels that overcomes the above mentioned problems.

SUMMARY OF INVENTION

In accordance with an aspect of the invention there is provided a method of forming a cross-linked polymer gel comprising mixing a first solution and a second solution, wherein the first solution comprises a cross-linking agent and a first chelating agent; the second solution comprises a displacing agent; wherein at least one of the first or second solutions contains an ionotropic polymer; and wherein: (a) the ionotropic polymer has a lower affinity for the cross-linking agent than the first chelating agent, and (b) the first chelating agent has a higher affinity for the displacing agent than the cross-linking agent. Preferably, the ionotropic polymer has a low affinity for the displacing agent.

This method uses competitive ligand exchange to control the release of a cross-linking agent to an aqueous solution of gel forming polymer. This is the first time that competitive ligand exchange has been used in the manufacture of ionically cross-linked hydrogels.

Embodiments of the invention are described in detail below with reference to the accompanying figures, in which:

FIG. 1. is a schematic diagram of the ligand exchange mechanism using a first and second chelator.

Figure 2A:
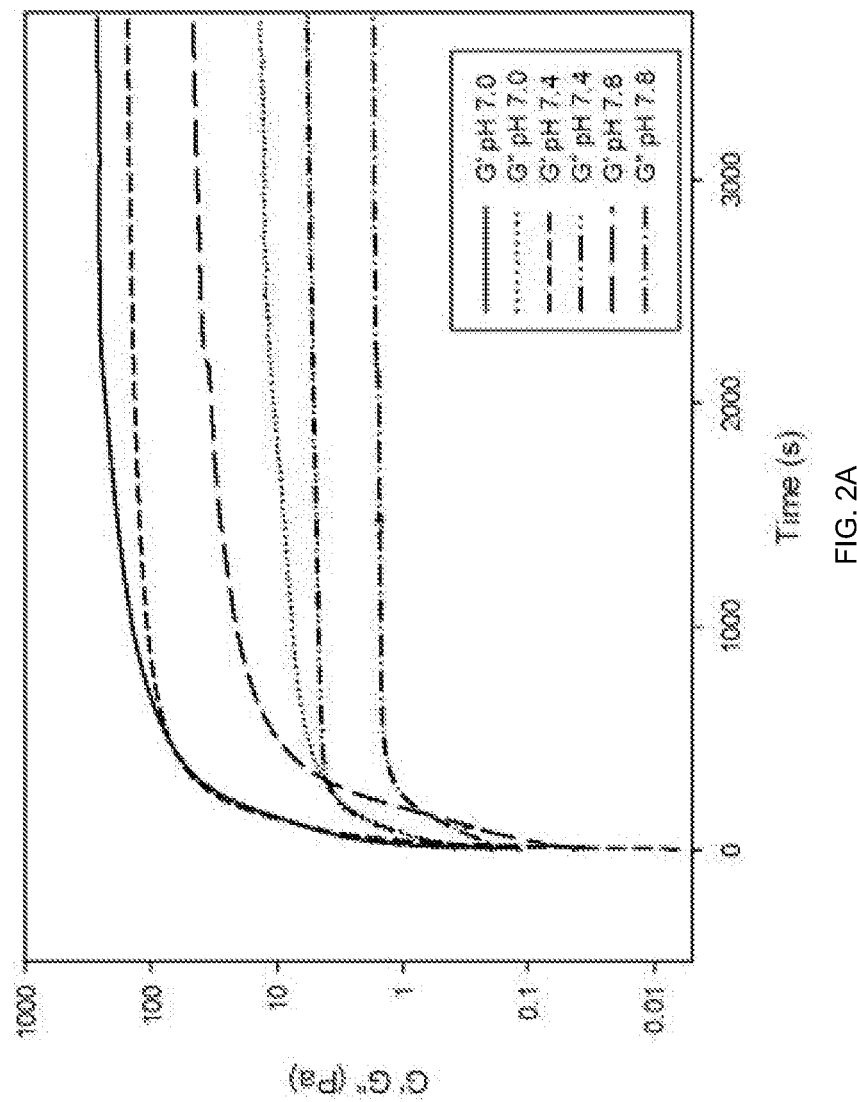
Figure 2B:
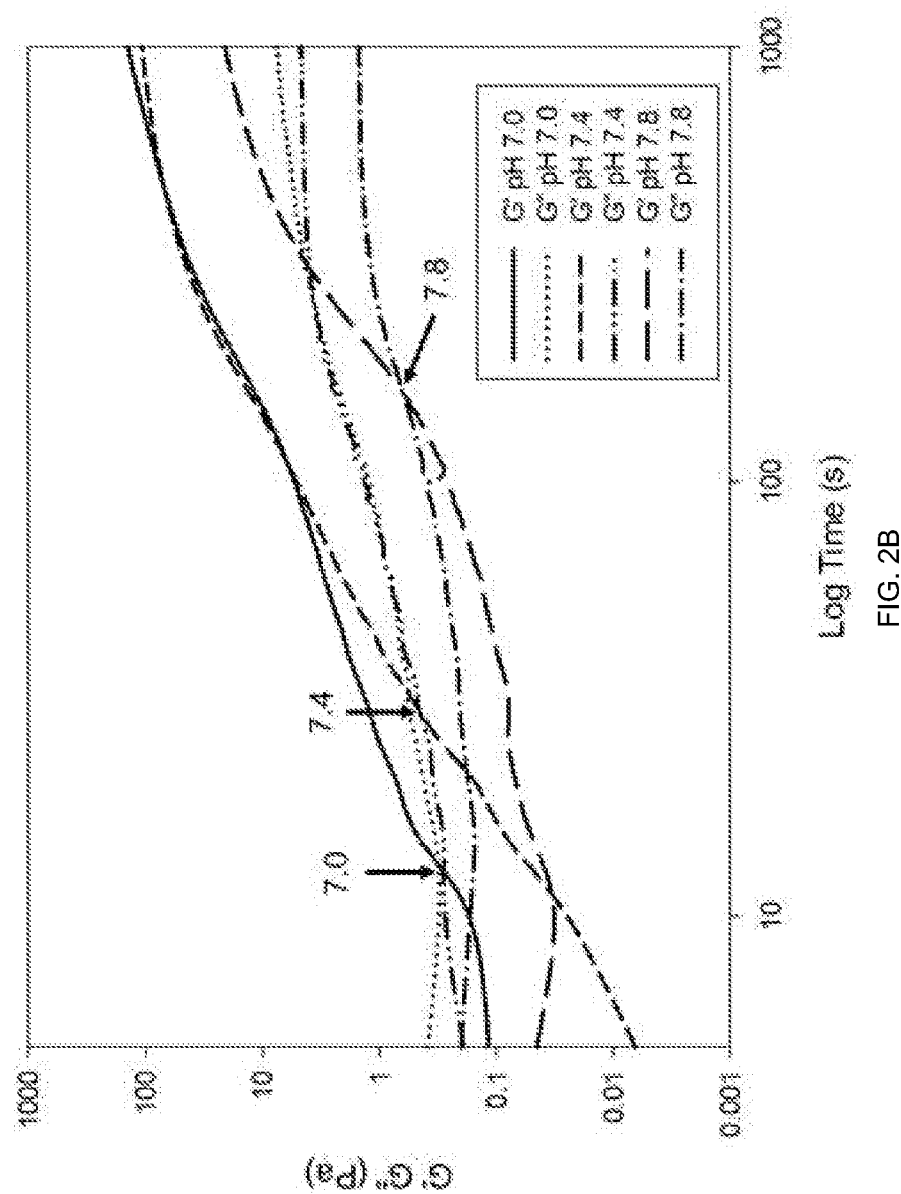

FIGS. 2A-2B shows the kinetics of gel formation as measured by rheology, showing the change in mechanical properties with time for alginate gels cross-linked using ligand exchange as a function of pH. FIG. 2A represents the rate of gel formation and storage and loss modulus as a function of time measured in seconds and shown in a linear time scale. FIG. 2B represents the same reaction and gel formation kinetics as shown in FIG. 2A displayed in a logarithmic time scale. Following mixing of two alginate solutions with defined pH, the storage and loss moduli were recorded as a function of time. Following mixing, the storage modulus increases more slowly with increasing pH. The point of gel formation is defined by the time-point at which G'=G". G' is storage modulus. G" is loss modulus. Rheological characterisation was performed using a Paar Physica MCR 300 Rheometer. A parallel plate geometry with serrated plate surfaces (PP50 serrated plate, diameter=50 mm) which provided minimal wall slip was used. Storage and loss moduli at a measuring gap of 1 mm were recorded as a function of time at a constant strain ($\gamma$) of 10%, angular frequency ($\omega$) of 1 rad s$^{-1}$, amplitude of 1 mrad and temperature of 25° C. Equal volumes (1.75 mL) of 2 component gels were measured onto the rheometer plate using a 5 mL pipette. The first component was placed directly onto the bottom plate, then the other was pipetted into it just prior to starting the measurement. Using this approach a lag time of approximately 30s resulted from the time of delivery of the second polymer solution to the start of data collection.

Figure 3B:
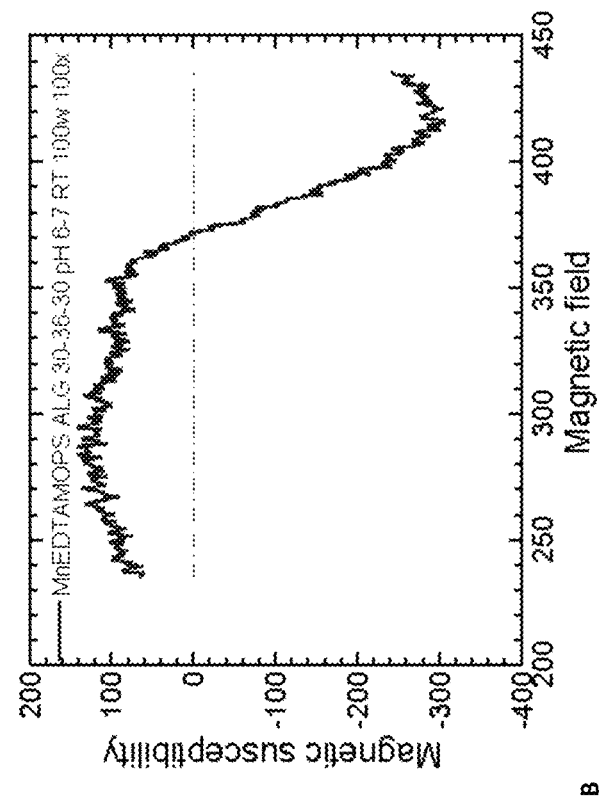
Figure 3A:
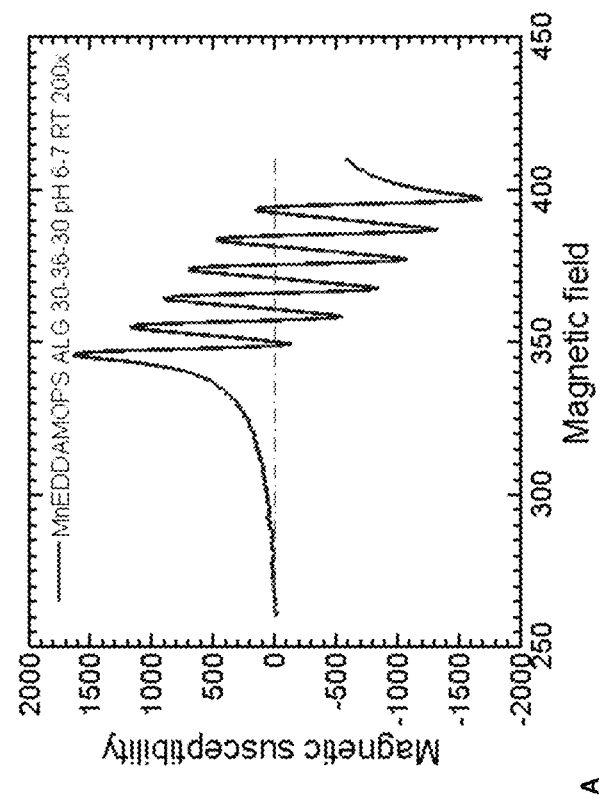
Figure 3D:
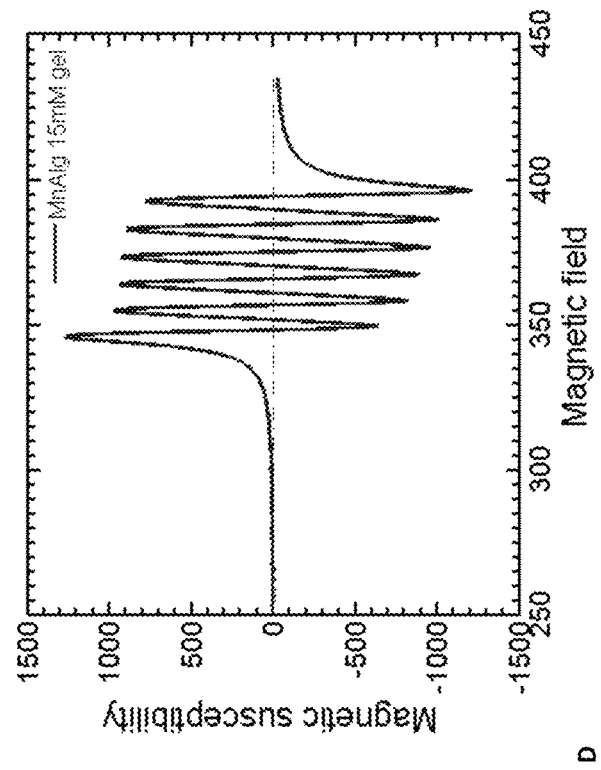
Figure 3C:
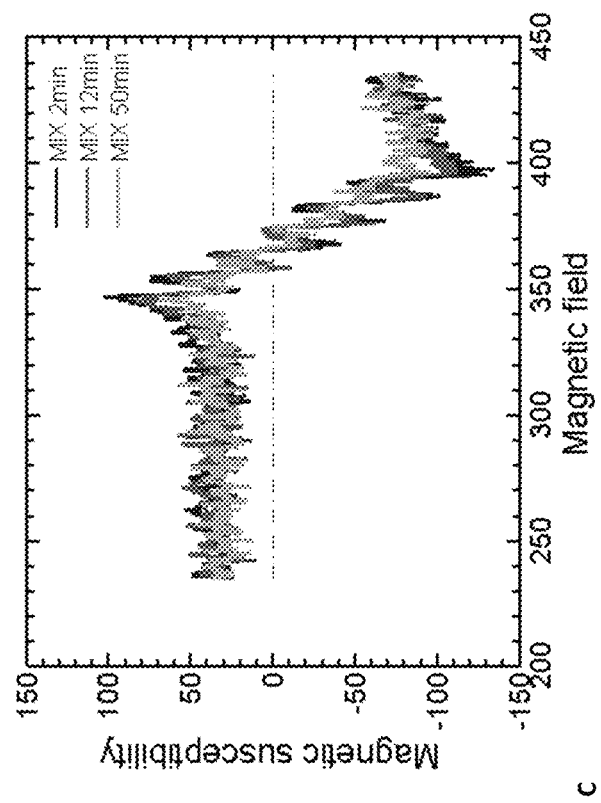

FIGS. 3A-3D shows EPR characterisation of gels formed using competitive ligand exchange. FIG. 3A and FIG. 3B are graphs that represent alginate samples with Mn-EDDA and Mn-EDTA respectively. FIG. 3C shows a graph shows spectra recorded following mixing of Ca-EDTA and Mn-EDDA at the indicated time points. FIG. 3D shows a graph shows spectra of alginate cross-linked with Mn$^{2+}$.

Figure 4:
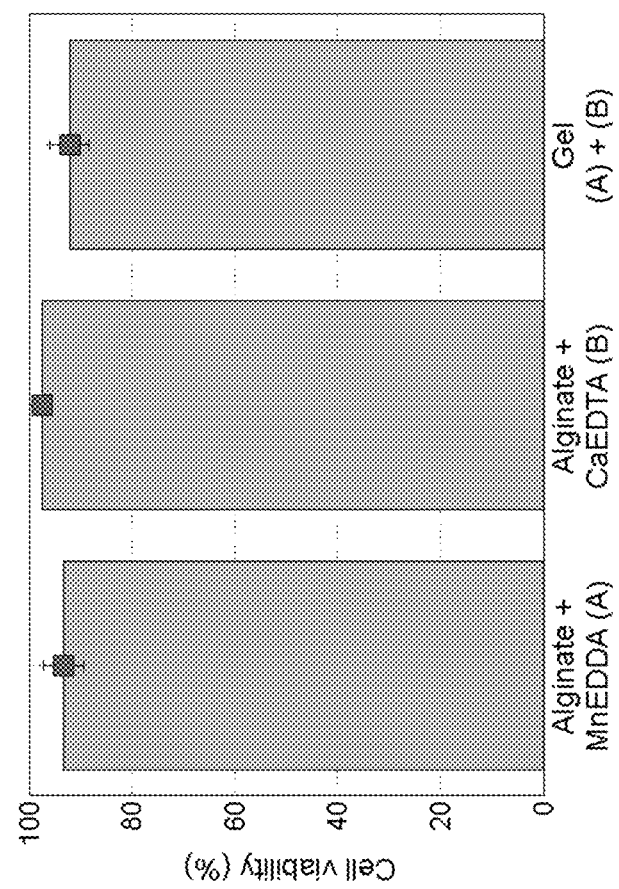

FIG. 4. shows the cell viability of MC3T3-E1 murine pre osteoblast cells incubated in precursor alginate samples containing CaEDTA and MnEDDA, prior to mixing and in the resulting bulk gel. Incubation time was 80 min. Live stain: Calcein-AM, Dead stain: Ethidium homodimer-1. Such results have also been seen using Zn.

Figure 5:
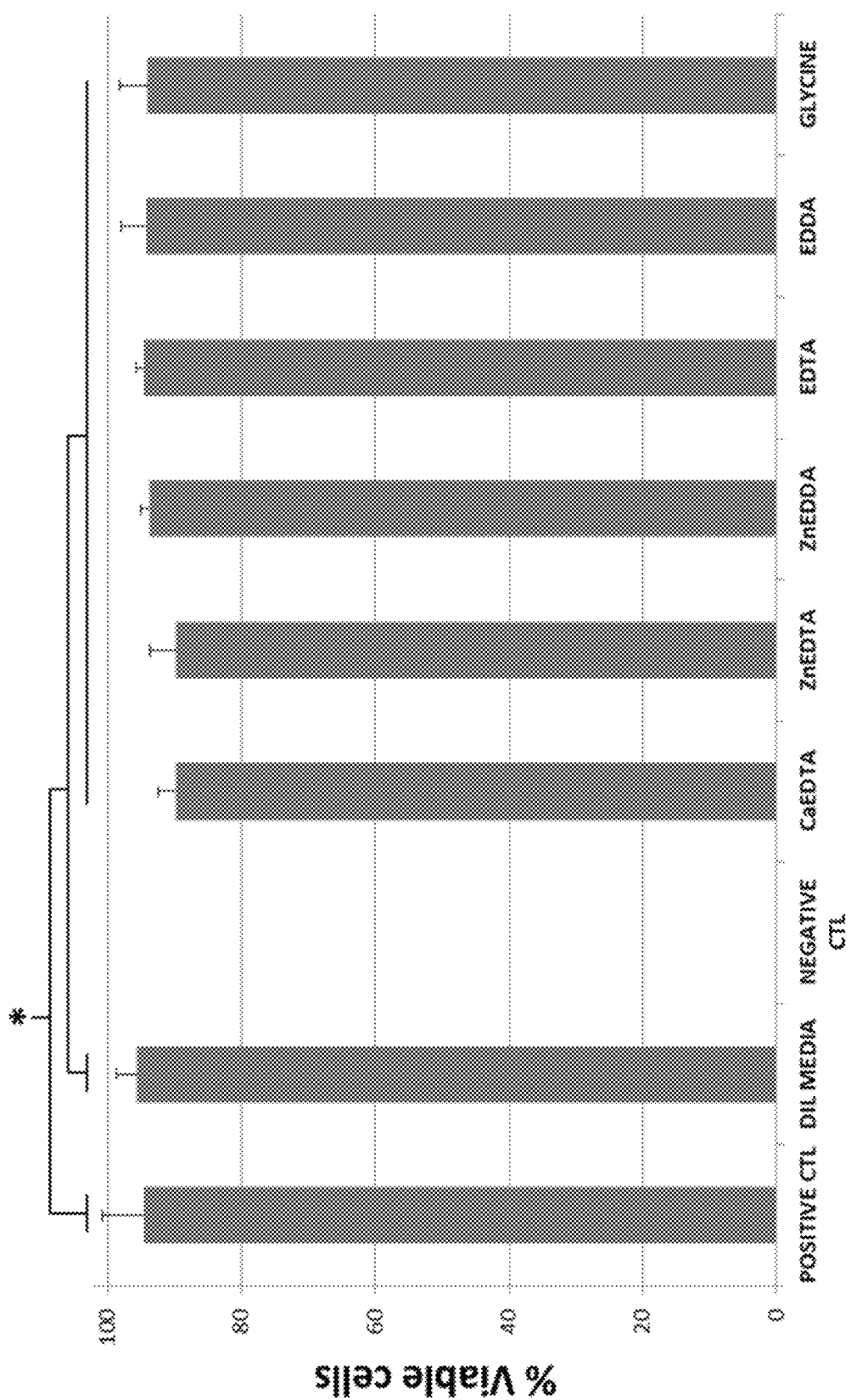

FIG. 5. shows the cell viability of MC3T3-E1 murine pre osteoblast cells as determined by toluidine blue infiltration following 2 h exposure to 60 mM concentrations of the indicated individual chemical components of the invention added to cell media. *No significant difference (P<0.05) in cell viability was observed for all experimental groups tested compared to positive (untreated) control cells. n=3, one way ANOVA with Holm-Sidak post hoc test applied. Negative control was cells treated with 0.1% triton-X. DIL Media is cell media diluted to the same extent (40%) as the test solutions with water.

Figure 6:
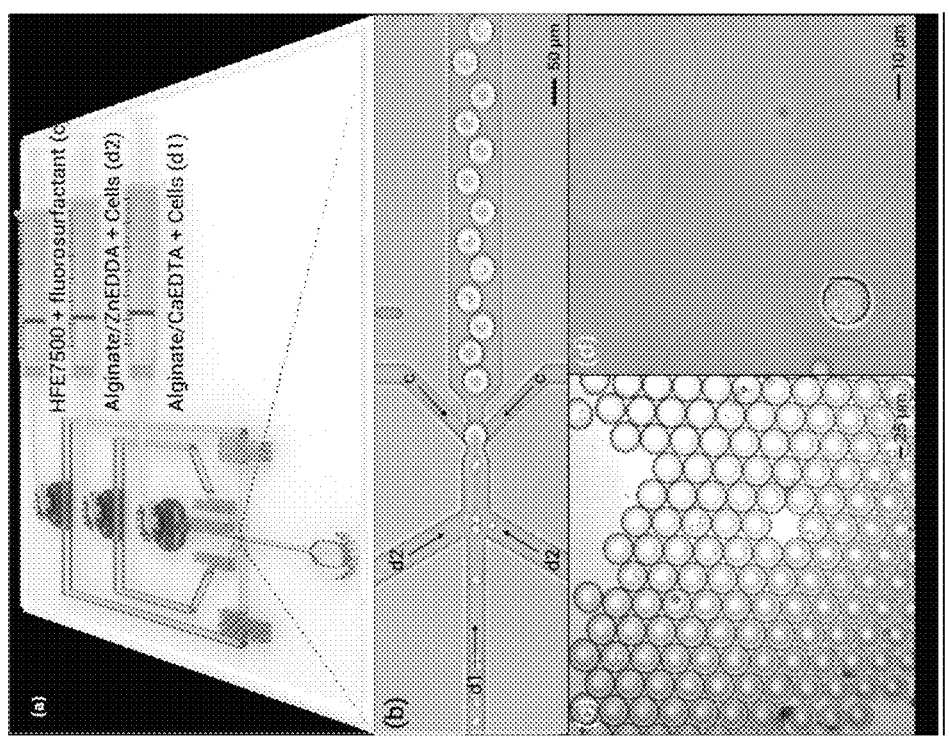

FIG. 6. shows an example of a microfluidic device in accordance with the present invention (FIG. 6a). FIG. 6b shows the micrograph of the region of the device at which encapsulation of cells occur. FIGS. 6c, and 6d show final gel beads containing encapsulated mammalian cells produced by this method.

Figure 7:
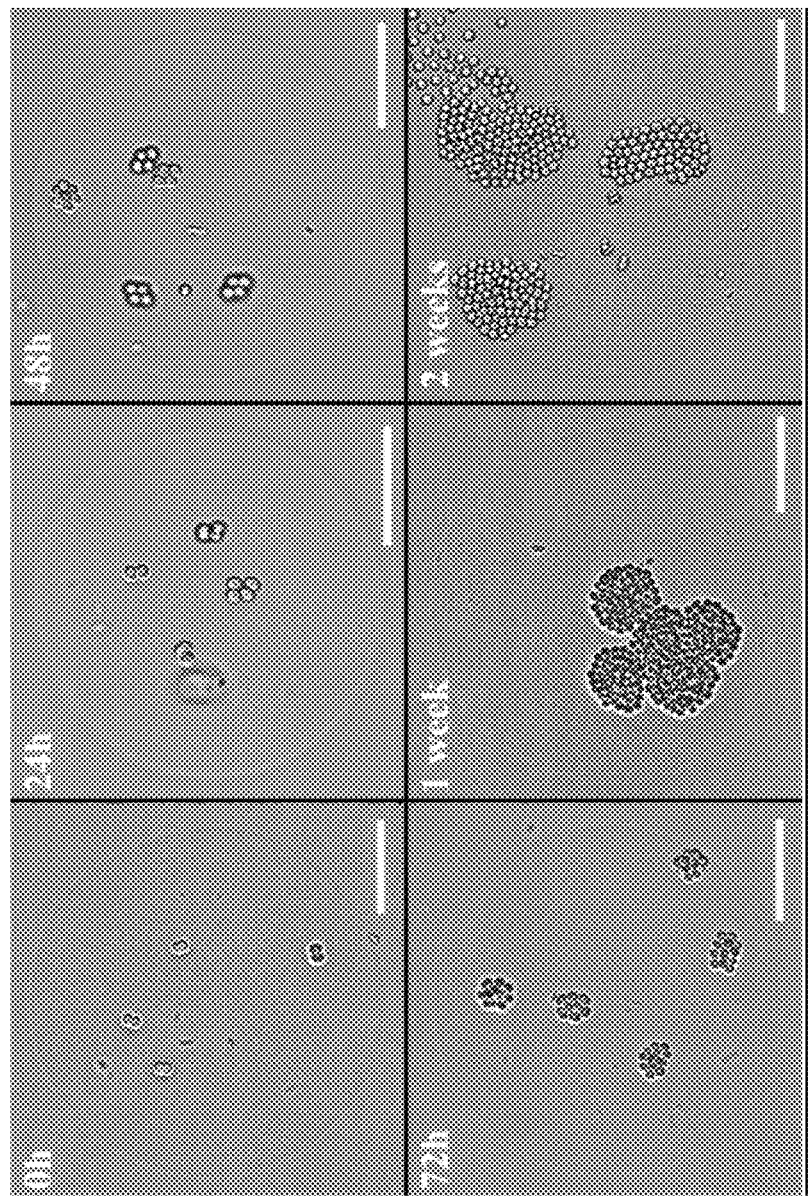

FIG. 7. shows micrographs of the cyanobacteria *Synechocystis* sp. PCC 6803 encapsulated in alginate hydrogel beads. All images are taken on a Leica SP5 confocal microscope with a 20× lens. Images are overlaid images of bright field and fluorescent images capturing the auto fluorescence of chlorophyll produced by the algae. Scale bars: 20 μm.

Figure 8:
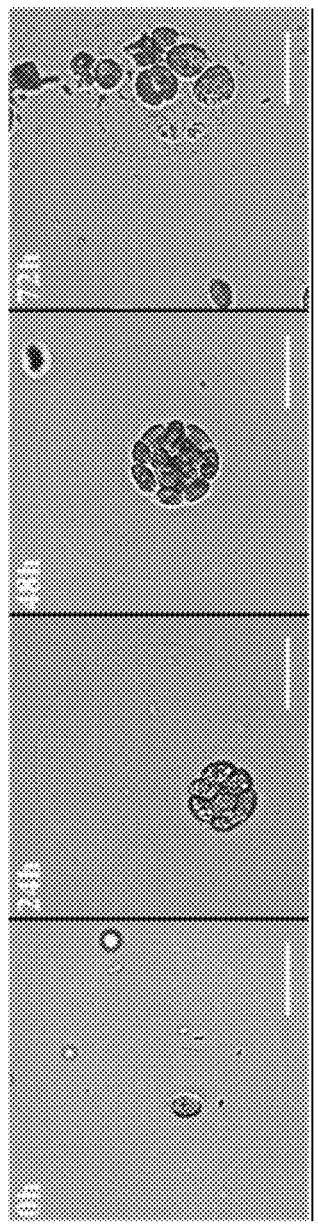

FIG. 8. shows micrographs of the algae *Chlamydomonas reinhardtii* CC-4532 encapsulated in alginate beads. Images of samples were taken 0(a), 24(b), 48(c) and 72(d) hours after encapsulation. All images are taken on a Leica SP5 confocal microscope with a 20× lens. Images are overlaid images of bright field and fluorescent images capturing the auto fluorescence of chlorophyll produced by the algae. Scale bars: 20 μm FIG. 9. shows the kinetics of gel formation as measured by rheology, showing the change in mechanical properties with time for an alginate-collagen gel (0.4% alginate, 1% collagen, pH 7.4) cross-linked using a two stage gelation. During the first stage (0-1800 s) the alginate is gelled using competitive ligand exchange which results in an increase in the storage (G') and loss (G") moduli. The gel point (the point at which G' and G" cross) is approximately 500 s. During the first stage, the temperature is maintained at 4° C., after which the temperature is rapidly increased and maintained at 37° C. for the remainder of the measurement. The increase in temperature triggers the gelation of the collagen, which occurs shortly after (approx. 100 s) the temperature increase. The gelation of collagen results in a further increase in G' and G" following an initial drop that occurred between 1800-1900 s in response to heating. Rheological characterisation was carried out as described in FIG. 2.

Figure 10:
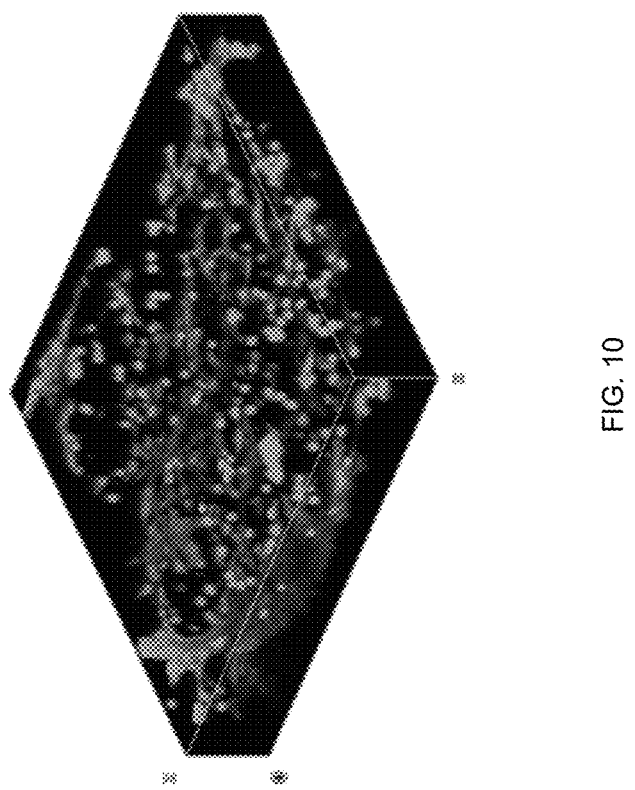

FIG. 10. shows a 3D rendering of a stack of fluorescent confocal light micrographs of MC3T3 E1 murine pre osteoblasts grown within an alginate-collagen hydrogel produced by a combination of ligand exchange crosslinking for the alginate and thermally triggered crosslinking for the collagen. The cells are well attached and spread within the gel following 7 days in culture. Green fluorescence was obtained from live cells stained with calcein-AM. Images were taken using a Leica SP5 confocal microscope. Field=775×775 μm.

DETAILED DESCRIPTION

The ionic polymer may be any polymer that can be cross-linked by ions to form a gel. Preferably metal ions are used for the cross-linking. Preferably the ions are multivalent cations. More preferably the ions are divalent cations. Ionotropic hydrogel-forming biopolymers, polyelectrolytes and synthetic polymers can be used. Such polymers are already known to the skilled person. Examples of ionic polymers that may be cross-linked using multivalent ions to form gels include, but are not limited to: polysaccharides, for example carrageenan, dextran, gellan, scleroglucan, chitosan, and derivatives thereof; water soluble polyphosphazenes, for example poly(bis(4-carboxyphenoxy)phosphazene); sodium polyacrylates; and polyamino acids. Preferably, the polymer used is alginate, pectin or polygalacturonate. More preferably, the polymer used is alginate.

The ionic polymer is preferably dissolved in a solvent, preferably an aqueous solvent, preferably water, more preferably distilled water. All other reactants, such as the displacing agent, cross-linking agent and chelating agent, are preferably water soluble.

Either the first solution or the second solution may comprise the ionotropic polymer. Alternatively, in a preferred embodiment, both solutions comprise an ionotropic polymer. The ionotropic polymer may be the same in each solution.

Alternatively, the first and second solutions may contain different ionotropic polymers. In this case, the resulting gel may be a mixture of different polymers.

Chelating agents, or chelators, are molecules that are able to sequester metal ions. Examples of ion chelating agents that can be used include, but are not limited to: synthetic chelators, for example EDTA, EGTA, EDDA, CDTA, PDTA, BAPTA, HPED, TES, TRIS, Tricine and NTA; complexones; crown ethers; histadines; nucleotides; nucleosides; porphyrins; phosphonates; citrates; siderophores; amino acids and peptides.

Any cross-linking agent may be used that forms a hydrogel with the selected ionotropic polymer. As used herein, the term cross-linking agent and gelling agent are used interchangeably. Preferably the cross-linking agent is a cross-linking ion. For example, if alginate is used as the polymer, multivalent cations, preferably divalent metal ions are used.

The displacing agent, also known as an exchange agent, may be any molecule capable of binding the first chelator in order to release the cross-linking agent. Thus, on mixing the first and second solutions, the displacing agent substitutes the cross-linking agent which is then rendered free to cross-link the ionotropic polymer, resulting in formation of the hydrogel. It is essential that the displacing agent has a higher affinity than the cross-linking agent for the chelating agent in order for the reaction to proceed. Preferably the displacing agent is an ion, more preferably a multivalent metal ion. Multivalent ions tend to have higher affinities for chelating agents than monovalent ions. Preferably the displacing agent has at least the same or higher valence as the cross-linking agent.

The cross-linking and displacing agent(s) are preferably multivalent ions, and the cross-linking agent ions are different to the displacing agent ions. In a preferred embodiment, the cross-linking agent and the displacing agent are independently selected from multivalent metal ions selected from the group consisting of $Ca^{2+}$, $Zn^{2+}$, $Fe^{2+}$, $Fe^{3+}$, $Al^{3+}$, $VO^{2+}$, $Cu^{2+}$, $Ba^{2+}$, $Ho^{3+}$, $Mg^{2+}$, $Mn^{2+}$, $Sr^{2+}$, $Zn^{2+}$, $Pb^{2+}$, $Co^{2+}$ and $Ni^{2+}$. Most preferably the cross-linking agent comprises $Ca^{2+}$. Most preferably, the displacing agent comprises a multivalent metal ion selected from the group consisting of $Zn^{2+}$, $Fe^{2+}$ and $Mn^{2+}$, most preferably $Zn^{2+}$. The cross-linking agent(s) need not be the same, i.e., there may be a mixture of cross-linking agents. Similarly, the displacing agent(s) need not be the same. Such mixed agents allow control of the gelling properties of the composition.

Preferably, the first chelating agent is selected from the group consisting of ethylenediamine-N,N'-disuccinic acid (EDDS), ethylenediaminetetraacetic acid (EDTA), ethylenediamine-N,N'-diacetic acid (EDDA), propylenediamine-N,N,N',N'-tetraacetic acid (PDTA), 1,2-cyclohexanedinitrilotetraacetic acid (CDTA), ethylene glycol tetraacetic acid (EGTA), 1,2-bis(o-aminophenoxy)ethane-N,N,N',N'-tetraacetic acid (BAPTA), hydroxyphenyl-ethylenediamine (HPED), nitrilotriacetic acid (NTA), porphyrin, citrate, phosphonates, and siderophores, more preferably ethylenediamine-N,N'-disuccinic acid (EDDS), ethylenediaminetetraacetic acid (EDTA), ethylenediamine-N,N'-diacetic acid (EDDA, propylenediamine-N,N,N',N'-tetraacetic acid (PDTA) and 1,2-cyclohexanedinitrilotetraacetic acid (CDTA). Even more preferably, the first chelating agent is selected from the group consisting of ethylenediaminetetraacetic acid (EDTA), propylenediamine-N,N,N',N'-tetraacetic acid (PDTA) and 1,2-cyclohexanedinitrilotetraacetic acid (CDTA), most preferably ethylenediaminetetraacetic acid (EDTA).

Preferably, the ionotropic polymer is selected from the group consisting of alginate, pectin, poly(galacturonate), carrageenan, dextran (and derivatives), gellan, scleroglucan, chitosan (and derivatives), water soluble polyphosphazenes, such as poly(bis(4-carboxyphenoxy)phosphazene), sodium polyacrylates, and polyamino acids, more preferably alginate, pectin and poly(galacturonate), most preferably alginate.

Published data on specific binding affinities is readily available, and can be used to select the combination of reagents for the gelling reaction. For example, Haug and Smidsrød, Acta Chemica Scandinavica, 1965, 19, 341, established the following series for divalent cations required to bring about gelation of alginate, with $Ba^{2+}$ requiring the lowest concentration and $Mg^{2+}$ the highest: Ba<Pb<Cu<Sr<Cd<Ca<Zn<Ni<Co<Mn, Fe<Mg. By comparing this series to the affinity series of well-studied ion chelating agents, such as EDTA and derivatives thereof, it becomes apparent that the alginate series may be quite different. For example, $Zn^{2+}$ and $Mn^{2+}$ bind weakly to alginate, but are strongly bound by EDTA (Log K=16.5 and 13.89 respectively). Such differences in affinities and the fact that the ions are held by physical, ionic interactions which are inherently dynamic, can therefore be exploited to control the availability of the gelling ion to the polyelectrolyte of interest.

For example, Table 1 shows a summary of several common chelating agents and their affinities to a selection of ions of interest for the formation of $Ca^{2+}$ cross-linked ionotropic gels. Log K values of selected cations and ligands at 25° C., background electrolyte concentration ($\mu$) of 0.1M and equilibrium quotient of [ML]/[M][L] unless otherwise stated are given, extracted from Smith et al. Standard Reference Data, Standard Reference Data Program, National Institute of Standards and Technology, U.S. Dept. of Commerce, Gaithersburg, Md. 2004 unless otherwise stated. The superscript x, y or z in each cell indicates if a gel will form if this cation-ligand combination occurs in combination with alginate i.e. if the strength of this complex is weaker than Ca-alginate.

TABLE 1

Cation-ligand combinations and their ability to form hydrogels with alginate

| | EDTA | EDDA | EGTA | EDDS | PDTA | CDTA | HBED | HPED |
|---|---|---|---|---|---|---|---|---|
| $Ca^{2+}$ | $10.65^z$ | $2.9^{x\&}$ | $10.86^z$ | $4.58^x$ | $11.55^z$ | $13.1^z$ | $9.29^y$ | $14.36^z$ |
| $Fe^{2+}$ | $14.3^z$ | $8.63^z$ | $11.8^z$ | — | $15.5^z$ | $18.9^z$ | — | $z$ |
| $Sr^{2+}$ | $8.72^x$ | $2.3^{x\&}$ | $8.42^x$ | $3.7^x$ | $9.58^x$ | $10.5^x$ | — | $x$ |
| $Fe^{3+}$ | 25.1 | — | 20.5 | $22.0^\$$ | 26.0 | 30.0 | 39.01 | 31.8 |
| $Al^{3+}$ | $16.4^x$ | — | $13.9^x$ | — | — | 19.5 | — | 25.78 |
| $VO^{2+}$ | 18.7 | 13.4 | $14.02^\#$ | — | — | $20.1^\$$ | — | — |
| $Ho^{3+}$ | $18.56^z$ | $8.42^y$ | $17.7^{\$z}$ | $13.6^z$ | $19.33^{z\$}$ | $21.0^{z\$}$ | $19.97^{z\$}$ | $z$ |

TABLE 1-continued

Cation-ligand combinations and their ability to form hydrogels with alginate

| | | | | | | | | |
|---|---|---|---|---|---|---|---|---|
| $Cu^{2+}$ | $18.78^x$ | $16.2^{x*}$ | $17.7^x$ | $18.4^x$ | $19.82^z$ | $22.0^z$ | $22.95^z$ | $23.67^z$ |
| $Mg^{2+}$ | $8.96^z$ | $3.95^z$ | $5.28^z$ | $6.01^z$ | $10.04^z$ | $11.0^z$ | $12.51^z$ | — |
| $Mn^{2+}$ | $13.89^z$ | $7.0^z$ | $12.2^z$ | $8.57^z$ | $15.0^z$ | $17.5^z$ | $14.78^z$ | — |
| $Ba^{2+}$ | $7.88^x$ | $1.2^{x\&}$ | $8.3^x$ | $3.0^x$ | $8.48^x$ | $8.58^x$ | — | — |
| $Zn^{2+}$ | $16.5^z$ | $11.1^z$ | $12.6^z$ | $13.4^{z\$}$ | $17.5^z$ | $19.3^z$ | $18.95^z$ | $19.57^z$ |
| $Co^{2+}$ | $16.45^z$ | $11.25^z$ | $12.3^z$ | $14.0^z$ | $17.4^z$ | $19.7^z$ | $19.43^z$ | $20.11^z$ |
| $Ni^{2+}$ | $18.4^z$ | $13.6^z$ | $13.5^z$ | $16.7^z$ | $19.6^z$ | $20.2^z$ | $20.07^z$ | $20.10^z$ |
| $Pb^{2+}$ | $18.0^x$ | $10.6^x$ | $14.6^x$ | $12.7^{x\$}$ | $18.92^{x\$}$ | $20.2^y$ | $18.24^x$ | $19.47^y$ |

| | TMDTA | TEDTA | DTPA | TRIS | TES | Glycine | Tricine |
|---|---|---|---|---|---|---|---|
| $Ca^{2+}$ | $7.18^y$ | $6.18^y$ | $10.75^z$ | $0.25^{x\square}$ | $x$ | $2.39^{x£}$ | $2.4^{xa}$ |
| $Fe^{2+}$ | $13.42^{z\$}$ | $11.57^{z\$}$ | $16.2^z$ | — | — | $4.3^c$ | — |
| $Sr^{2+}$ | $5.24^{x\$}$ | $5.94^{x\$}$ | $9.79^x$ | $0.11^{x\square}$ | — | — | — |
| $Fe^{3+}$ | $21.4^\$$ | $20.41^\$$ | $27.7$ | — | — | — | — |
| $Al^{3+}$ | $16.27^{x\$}$ | — | $18.6^x$ | — | — | — | — |
| $VO^{2+}$ | — | — | $16.31$ | — | — | — | — |
| $Ho^{3+}$ | $14.92^{z\$}$ | $14.67^z$ | $22.79^z$ | — | — | — | — |
| $Cu^{2+}$ | $18.8^x$ | $16.45^x$ | $21.2$ | $4.05^x$ | $3.9^x$ | — | $7.3^{xa}$ |
| $Mg^{2+}$ | $6.24^z$ | $4.66^z$ | $9.27^z$ | $0.3^\square$ | — | $2.67^{z£}$ | $1.2^{za}$ |
| $Mn^{2+}$ | $10.01^z$ | $10.05^z$ | $15.2^z$ | — | — | $3.41^{z£}$ | $2.7^{za}$ |
| $Ba^{2+}$ | $3.86^{x\$}$ | $5.34^{x\$}$ | $8.74^x$ | $0.02^\square$ | — | — | — |
| $Zn^{2+}$ | $15.22^z$ | $13.99^z$ | $18.2^z$ | $2.27^z$ | $2.08^z$ | $3.04^{z£}$ | $5.59^{zb}$ |
| $Co^{2+}$ | $15.51^z$ | $13.93^z$ | $18.8^z$ | $1.73$ | $2.07$ | $2.26^£$ | $4.49^b$ |
| $Ni^{2+}$ | $18.21^z$ | $15.56^z$ | $20.1^z$ | $2.63$ | $3.35^\$$ | $2.59^£$ | $5.51^b$ |
| $Pb^{2+}$ | $13.59^x$ | $13.69^x$ | $18.8^x$ | — | — | — | $4.25^{xb}$ |

*30° C.,
µ 0.5, $20° C.,
□µ 1.0
&Taken from: Ewin and Hill. A Thermometric Titrimetric Study of the Complexation of Alkaline-earth Metals by Linear Poly(aminocarboxylic) Acids. J. Chem Soc. Dalton & Trans. 1983 865-868
£Taken from: Kiss, Sovago and Gergely. Critical Survey of Stability Constants of Complexes of Glycine. Pure Appl. Chem. 1991: 63(4): 597-638. All values at 35° C.
aTaken from: Good et al. Hydrogen Ion Buffers for Biological Research. Biochemistry. 1966; 5(2): 467-477
bTaken from: Ahmed. Formation Constants of Ternary Complexes Involving Some Metal Ions, Tricine, Dicarboxylic Amino Acids, as Well as N-(2-Acetamido)iminodiacetic Acid and 3-Amino-5-mercapto-1,2,4-triazole J. Chem. Eng. Data. 2003; 48(2): 272-276
cTaken from T. E. Furia, CRC Handbook of Food Additives, Taylor & Francis, 2nd edn, 1973.
Key:
xStrong gelation (cross-links alginate)
yGelation (partially cross-links alginate)
zNo gelation, stable with alginate (displacing agent does not release cross-linking agent-no cross-linking)

An alginate solution containing a Ca-EDTA complex above pH5 will not form a gel, nor will a solution of alginate with a sufficiently low concentration of $Zn^{2+}$ ions. Sufficiently low means approximately 9 mM or less, although the skilled person will understand that the exact amount of ions required will depend on the type and concentration of alginate used. At a pH lower than 5, the affinity for $Ca^{2+}$ will be higher for alginate than for EDTA, therefore the polymer will crosslink. When the two solutions are mixed together, a gel will form above pH 5. This is due to the fact that $Ca^{2+}$ ions chelated by EDTA will quickly be displaced and exchanged with the free $Zn^{2+}$ ions, since the affinity of EDTA for $Zn^{2+}$ is much greater than $Ca^{2+}$. Calcium ions will be released, and since free $Ca^{2+}$ binds strongly to alginate, a gel will quickly form upon mixing. Here, $Zn^{2+}$ acts as the displacing agent as it is exchanged for the cross-linking ion ($Ca^{2+}$) in the Ca-EDTA complex. By manipulating pH, it is possible to control when gelation occurs. Below pH 5, alginate will have a higher affinity for $Ca^{2+}$ than EDTA and will therefore crosslink the alginate. The skilled person will understand that this value will change depending on chelator and/or ion, and that the pH used will also depend on the Pka value of the polymer. At strongly alkaline pH, if Zn is used it will tend to precipitate ZnOH.

In a preferred embodiment, the ionotropic polymer is alginate, $Ca^{2+}$ is used as the crosslinking agent, and $Zn^{2+}$, $Fe^{2+}$ or $Mn^{2+}$ is used as the displacing agent. The inventors have found that 1% alginate solution containing $ZnCl_2$, $FeSO_4$ or $MnCl_2$ efficiently forms a gel when minimum concentrations of approximately 9 mM $Zn^{2+}$+12 mM $Fe^{2+}$ or $Mn^{2+}$ are used as displacing agent, and $Ca^{2+}$ is used as the crosslinking agent. When this solution is mixed with a 1% alginate solution containing Ca-EDTA, a gel is formed within a few seconds providing the concentration of Ca-EDTA is sufficiently high to provide a final concentration of at least 3 mM of $Ca^{2+}$. This observation was also repeated when a Ca-EDTA containing alginate solution was gelled upon addition of aqueous $Zn^{2+}$ $Fe^{2+}$ or $Mn^{2+}$ solutions or when aqueous Ca-EDTA was added to Zn- Fe- or Mn-alginate solutions at concentrations that are too weak to gel the alginate (i.e. below approximately 9 mM $Zn^{2+}$, or 12 mM for $Fe^{2+}$ or $Mn^{2+}$), but above the critical $Ca^{2+}$ concentration of 3 mM. Gel formation in this system is determined by the kinetics of the exchange reaction after the two solutions are mixed and follows the following reaction: $Zn^{2+}/Fe^{2+}/Mn^{2+}$+ Ca-EDTA→Zn/Fe/Mn-EDTA+$Ca^{2+}$.

Hydrogels formed using the approach described above form rather rapidly. Therefore, in a particularly preferred embodiment, the second solution further comprises a second chelating agent capable of chelating the displacing agent. Preferably, the second chelating agent i) has a higher affinity for the displacing agent than the polymer; ii) has a lower affinity for the cross-linking agent than the polymer; and iii) has a lower affinity for the displacing agent than the cross-linking ion chelating agent, so that the reaction can still proceed.

The displacing agent may also be chelated to prevent cross-linking of the polymer. However the second chelator used for this purpose must have a lower affinity for the cross-linking agent than the polymer itself to allow cross-linking to occur. The polymer has a lower affinity for the displacing agent than the displacing ion chelator. Reaction conditions can be modified to control the release of the cross-linking agent by means of modifying the pH and temperature. This is particularly advantageous because it allows good control over the gelation rate. Furthermore, this approach may be used in defined and constant conditions of pH which may further be neutral or physiological (pH 7.4) and is therefore highly amenable to biomedical applications. The reaction proceeds with a consumption of $H^+$, therefore a small pH increase often occurs. To maintain a constant pH a buffer may be used. FIG. 1 shows a schematic diagram of ligand exchange gelation using two chelating agents.

Preferably, the first and second chelating agents are independently selected from the group consisting of ethylenediamine-N,N'-disuccinic acid (EDDS), ethylenediaminetetraacetic acid (EDTA), ethylenediamine-N,N'-diacetic acid (EDDA), propylenediamine-N,N,N',N'-tetraacetic acid (PDTA), 1,2-cyclohexanedinitrilotetraacetic acid (CDTA), ethylene glycol tetraacetic acid (EGTA), 1,2-bis(o-aminophenoxy)ethane-N,N,N',N'-tetraacetic acid (BAPTA), hydroxyphenyl-ethylenediamine (HPED), nitrilotriacetic acid (NTA), 2-[(2-Hydroxy-1,1-bis(hydroxymethyl)ethyl)amino]ethanesulfonic acid, N-[Tris(hydroxymethyl)methyl]-2-aminoethanesulfonic acid (TES), 2-Amino-2-(hydroxymethyl)-1,3-propanediol (TRIS), N-[Tris(hydroxymethyl)methyl]glycine (Tricine), porphyrin, citrate, phosphonates, amino acids, peptides and siderophores, more preferably ethylenediamine-N,N'-disuccinic acid (EDDS), ethylenediaminetetraacetic acid (EDTA), ethylenediamine-N,N'-diacetic acid (EDDA, propylenediamine-N,N,N',N'-tetraacetic acid (PDTA), 1,2-cyclohexanedinitrilotetraacetic acid (CDTA) and aminoacetic acid (glycine).

More preferably, the first chelating agent is selected from the group consisting of ethylenediaminetetraacetic acid (EDTA), ethylenediamine-N,N'-disuccinic acid (EDDS), propylenediamine-N,N,N',N'-tetraacetic acid (PDTA) and 1,2-cyclohexanedinitrilotetraacetic acid (CDTA), even more preferably ethylenediaminetetraacetic acid (EDTA).

More preferably, the second chelating agent is selected from the group consisting of ethylenediamine-N,N'-disuccinic acid (EDDS), aminoacetic acid (glycine) and ethylenediamine-N,N'-diacetic acid (EDDA), even more preferably ethylenediamine-N,N'-diacetic acid (EDDA) or aminoacetic acid (glycine) or mixtures thereof.

Particularly preferred combinations of reagents are listed in the table below. Use of $Zn^{2+}$ as the displacing agent is particularly preferred. However, other ions may be used that behave in a similar way, such as $Co^{2+}$ and $Ni^{2+}$. The ionotropic polymer may be present in the first and/or second solution. Preferably, the ionotropic polymer is present in both the first and second solutions.

| | Ionotropic polymer | Cross-linking agent | First chelating agent | Displacing agent | Second chelating agent |
|---|---|---|---|---|---|
| 1 | Alginate | $Ca^{2+}$ | EDTA | $Zn^{2+}$ | EDDA |
| 2 | Alginate | $Ca^{2+}$ | EDTA | $Mn^{2+}$ | EDDA |
| 3 | Alginate | $Ca^{2+}$ | EDTA | $Fe^{2+}$ | EDDA |
| 4 | Alginate | $Ca^{2+}$ | CDTA | $Zn^{2+}$ | EDDA |
| 5 | Alginate | $Ca^{2+}$ | PDTA | $Zn^{2+}$ | EDDA |
| 6 | Alginate | $Ca^{2+}$ | CDTA | $Zn^{2+}$ | EDDS |
| 7 | Alginate | $Ca^{2+}$ | PDTA | $Zn^{2+}$ | EDDS |
| 8 | Alginate | $Ca^{2+}$ | EDTA | $Zn^{2+}$ | Glycine |
| 9 | Alginate | $Ca^{2+}$ | EDDS | $Zn^{2+}$ | Glycine |
| 10 | Pectin | $Ca^{2+}$ | PDTA | $Zn^{2+}$ | EDDA |
| 11 | Pectin | $Ca^{2+}$ | CDTA | $Zn^{2+}$ | EDDA |
| 12 | Pectin | $Ca^{2+}$ | PDTA | $Mn^{2+}$ | EDDS |
| 13 | Pectin | $Ca^{2+}$ | CDTA | $Mn^{2+}$ | EDDS |
| 14 | Pectin | $Ca^{2+}$ | EDTA | $Zn^{2+}$ | EDDA |
| 15 | Pectin | $Ca^{2+}$ | EDTA | $Zn^{2+}$ | EDDS |
| 16 | Poly(galacturonate) | $Ca^{2+}$ | PDTA | $Zn^{2+}$ | EDDA |
| 17 | Poly(galacturonate) | $Ca^{2+}$ | CDTA | $Zn^{2+}$ | EDDA |
| 18 | Poly(galacturonate) | $Ca^{2+}$ | PDTA | $Mn^{2+}$ | EDDS |
| 19 | Poly(galacturonate) | $Ca^{2+}$ | CDTA | $Mn^{2+}$ | EDDS |

EDTA: Ethylenediaminetetraacetic acid
EDDA: Ethylenediamine-N,N'-diacetic acid
PDTA: Propylenediamine-N,N,N',N'-tetraacetic acid
CDTA: 1,2-cyclohexanedinitrilotetraacetic acid
EDDS: Ethylenediamine-N,N'-disuccinic acid Preferably, the pH ranges used are as follows:

| Polymer | pH range | Cross-linking agent | Cross-linking chelator (first chelator) | Displacing agent | Displacing agent chelator (second chelator) |
|---|---|---|---|---|---|
| Alginate | 5-8 | $Ca^{2+}$ | EDTA | $Zn^{2+}$ | EDDA |
| Alginate | 5-8 | $Ca^{2+}$ | EDTA | $Mn^{2+}$ | EDDA |
| Alginate | 5-8 | $Ca^{2+}$ | EDTA | $Fe^{2+}$ | EDDA |
| Alginate | 4-7 | $Ca^{2+}$ | CDTA | $Zn^{2+}$ | EDDS |
| Alginate | 4-7 | $Ca^{2+}$ | CDTA | $Zn^{2+}$ | EDDA |
| Alginate | 6.5-9.5 | $Ca^{2+}$ | EDTA | $Zn^{2+}$ | Glycine |
| Alginate | 9-11 | $Ca^{2+}$ | EDDS | $Zn^{2+}$ | Glycine |
| Pectin | 4-6 | $Ca^{2+}$ | PDTA | $Zn^{2+}$ | EDDA |
| Pectin | 4-6 | $Ca^{2+}$ | CDTA | $Zn^{2+}$ | EDDA |
| Pectin | 4-6 | $Ca^{2+}$ | PDTA | $Mn^{2+}$ | EDDS |
| Pectin | 4-6 | $Ca^{2+}$ | CDTA | $Mn^{2+}$ | EDDS |
| Poly(galacturonate) | 5-8 | $Ca^{2+}$ | PDTA | $Zn^{2+}$ | EDDA |
| Poly(galacturonate) | 5-8 | $Ca^{2+}$ | CDTA | $Zn^{2+}$ | EDDA |
| Poly(galacturonate) | 5-8 | $Ca^{2+}$ | PDTA | $Mn^{2+}$ | EDDS |
| Poly(galacturonate) | 5-8 | $Ca^{2+}$ | CDTA | $Mn^{2+}$ | EDDS |

Introduction of a secondary chelator has several benefits. Use of a second chelating agent allows a high concentration of exchange ions, in excess of that necessary to fully cross-link the polymer, preferably alginate, when unchelated, to be applied in solution without forming a gel. This allows complete gelling of the polyelectrolyte or polymer forming a strong gel, or indeed allows adjustment of the reaction to achieve any degree of gelation. Secondly, it allows for better control of pH. Aqueous solutions of free exchange ions such as $Zn^{2+}$, $Fe^{2+}$ and $Mn^{2+}$ tend to be acidic, and will likely precipitate hydroxide salts upon an increase in pH. However, this is prevented when the ion is fully chelated, which allows the polymer solution to be buffered at a desired, for example physiological, pH. Also, the rate of the exchange reaction which in turn determines the kinetics of gel formation will also strongly depend on the pH since the relative affinities between the ions and the chelators and the polymer will vary as a function of pH.

A combination of EDTA/EDDA works well for $Ca^{2+}$ crosslinking of alginate at pH 5-8, and so any polymer with a similar affinity for $Ca^{2+}$ compared to alginate will work well, for example pectin and ι-carrageenan.

The method of the present invention is preferably carried out between 5° C. and 40° C., more preferably between 10° C. and 30° C. Extreme temperatures of below 0° C. and above 100° C. should be avoided. Preferably the method is carried out at a pH of 4 to 9, preferably 6 to 8, preferably 6.5 to 7.5, preferably 7.2 to 7.4. The pH may be varied, preferably within these ranges, during the course of the gelling reaction, and/or to initiate it.

Preferably, the concentration of the first chelating agent in the first solution is in the range of 2 mM to 200 mM, preferably 3 mM to 180 mM, more preferably 4 mM to 120 mM, further preferably 5 mM to 110 mM, even more preferably 10 mM to 110 mM, most preferably 15 mM to 100 mM. Preferably, the concentration of the second chelating agent, if used, is in the range of 2 mM to 200 mM, preferably 3 mM to 180 mM, more preferably 4 mM to 120 mM, further preferably 5 mM to 110 mM, even more preferably 10 mM to 110 mM, most preferably 15 mM to 100 mM Preferably, the concentration of the cross-linking agent in the first solution is in the range of 2 mM to 200 mM, preferably 3 mM to 180 mM, more preferably 4 mM to 120 mM, further preferably 4 mM to 110 mM, even more preferably 7 mM to 110 mM, most preferably 12 mM to 100 mM.

Preferably, the concentration of the displacing agent in the first solution is in the range of 2 mM to 200 mM, preferably 3 mM to 180 mM, more preferably 4 mM to 120 mM, further preferably 4 mM to 110 mM, even more preferably 7 mM to 110 mM, most preferably 12 mM to 100 mM. The displacing agent should be of comparable concentration to the cross-linking agent. The amount of displacing agent will determine the amount of crosslinking agent released upon mixing.

At the minimum concentration, the hydrogel will not be fully cross-linked, whereas an excess of cross-linking ion will give a strong gel. For example, a concentration of ~4 mM to 120 mM $Ca^{2+}$ in the final gelling solution can be used to form an alginate hydrogel. When using a 1% alginate solution, the hydrogel will not be fully cross-linked at ~4 mM and will not fully cross-link until the concentration is approximately ~30 mM. Use of 120 mM of the crosslinking ion and displacing ion will give 60 mM in the final preparation which is an excess as it is more than enough to fully gel the alginate. With alginate solutions, the specific concentration at which full cross-linking occurs depending on the number of α-L-guluronate (G) residues, also known as G content. The skilled person will understand that the exact concentrations of crosslinking agent and displacing agent will depend on the polymer used and the polymer concentration used. For example, alginate polymers at a concentration above 1% will saturate at a higher concentration of crosslinking agent.

Preferably, the ionotropic polymer is in a concentration in the mixed solution in the range of 0.1-20 wt/vol %, for alginate preferably 0.5-5 wt/vol %.

Preferably, the method of the present invention is carried out by dissolving the polymer, such as alginate, in a solvent, preferably water. Next an aqueous solution of the cross-linking ion (for example $Ca^{2+}$) is prepared, the concentration of which is typically 0.5-1M. When using $Ca^{2+}$ as the cross-linking ion, usually this solution is $CaCl_2$. An aqueous solution of the chelating agent is prepared (for example EDTA solution is prepared at pH>5, using NaOH to dissolve, preferably at 0.5 M at pH 8). Optionally, an aqueous buffer may be included that is active in the desired range. For example, MOPS (3-(N-morpholino)propanesulfonic acid) can be used (pH 6.5-7.9) or HEPES (4-(2-hydroxyethyl)-1-piperazineethanesulfonic acid) (pH 6.8-8.2) at a concentration of 1M. MOPS is particularly preferred since this buffer binds negligible amounts of the ions of interest.

The cross-linking agent and chelating agent, and buffer solution if used, are mixed together. When mixing $Ca^{2+}$, EDTA and buffer solutions the molar ratio should preferably be between 1:1:0-1:1:1, and Ca and EDTA should preferably be equal to each other. The pH is preferably adjusted to between 5-9, preferably 6.5-7.5. The pH is preferably adjusted before mixing with the polymer solution. The polymer solution and cross-linking agent/chelating agent/buffer solutions are mixed in proportions. Preferably, a solution having 1% alginate concentration and between 12-120 mM CaEDTA concentration, more preferably 15-100 mM CaEDTA concentration, is obtained.

Next, a second (polymer) solution is produced. The solution preferably comprises a second chelating agent, the displacing ion, and optionally, an ionotropic polymer. For example, an alginate-ZnEDDA solution. Preferably, the polymer is alginate dissolved to a concentration of about 3 wt/vol % in water. Next an aqueous solution of the displacing ion is prepared, for example an aqueous $Zn^{2+}$ solution, the concentration of which is preferably 0.5-1M. Most preferably, an aqueous solution of $Zn(CH_3CO_2)_2$ is used. Next an aqueous solution of the second chelator is provided. Preferably this is an aqueous EDDA solution at pH>5, using NaOH to dissolve, typically 0.5M and at pH 8. Optionally, an aqueous buffer active in the desire range can be used. Preferably this can be MOPS (pH 6.5-7.9) or HEPES (pH 6.8-8.2) at a concentration of 1 M.

The displacing agent and second chelator, and buffer if used, are mixed. Preferably, $Zn^{2+}$, EDDA and buffer solutions are mixed at a molar ratio of between 6:5:0-6:5:6. The EDDA should preferably be in a slight excess to $Zn^{2+}$, preferably at a 6:5 ratio. The pH should be adjusted, preferably to between 5-9, and more preferably 6.5-7.5. The pH is preferably adjusted before mixing with the polymer solution. The polymer solution and displacing agent/second chelating agent/buffer solutions are mixed. Preferably, a solution having 1% alginate concentration and between 12-120 mM, more preferably 15-100 mM CaEDTA concentration, ZnEDDA concentration is obtained.

To make the hydrogel, preferably approximately equal proportions of the resulting polymer solutions are mixed. Preferably alginate-CaEDTA and alginate-ZnEDDA, are mixed together.

The same gelation principle is applied to two further ionotropic polymers, pectin and poly(galacturonate). Poly (galacturonate) has a higher affinity for $Ca^{2+}$ than alginate and therefore mixing Ca-EDTA with this polymer forms a weak gel. Alternative chelators propylenediamine-N,N,N', N'-tetraacetic acid (PDTA) and 1,2-cyclohexanedinitrilotetraacetic acid (CDTA), have both been found to form a stable solution with $Ca^{2+}$ and poly(galacturonate), thus forming stable gels, upon mixing with an exchange ion such as $Zn^{2+}$ and exchange ion chelates such as Zn-EDDA or Mn-EDDS. Using CDTA and PDTA instead of EDTA lowers the pH range possible to make useful gels of alginate and pectin to pH 4-7.

To verify the proposed gel formation mechanism, electron paramagnetic spectroscopy (EPR) was also used to monitor the reaction Ca-EDTA to Mn-EDTA in the presence of alginate (FIGS. 3A-3D). $Mn^{2+}$ was chosen for this experiment since it is a paramagnetic ion and is suitable for EPR measurements. The $Mn^{2+}$ contained in the Mn-EDDA appeared much more flexible than in the Mn-EDTA complex (see FIGS. 3A and 3B). Upon mixing approximately equal proportions of alginate containing Ca-EDTA and alginate containing Mn-EDDA, the EPR spectra shifted from resembling the Mn-EDDA structure to resembling the Mn-EDTA structure (FIG. 3C) and did not achieve an EPR spectra similar to Mn-Alginate (FIG. 3D). This is direct evidence that the $Mn^{2+}$ was exchanged from EDDA to EDTA and did not become associated with the alginate, which was cross-linked by the liberated $Ca^{2+}$. A characteristic Mn-alginate spectra was also not recorded for the Mn-EDDA or Mn-EDTA complexes in the presence of alginate, indicating the $Mn^{2+}$ was entirely chelated by the ligands.

In another aspect of the invention there is provided a cross-linked polymeric gel obtainable or obtained by the controllable process described above. Preferably the cross-linked polymeric gel comprises a gelled ionotropic polymer, a cross-linking agent, a first chelating agent, a second chelating agent and a displacing agent, and water.

The hydrogels of the present invention have numerous advantages over prior art hydrogels. For example, the hydrogels formed according to the methods of the present invention do not contain any solid components (excluding the gel itself) prior to or after gelling. As such the gel remains optically transparent throughout gelling. Furthermore, no water or gas is produced in the gelling reaction. This is a major limitation of the GDL-$CaCO_3$ method, whereby it is difficult to form large gels and gels of high polymer content due to water formation and subsequent syneresis, and the $CO_2$ produced as a side product results in bubbles trapped in the gel. Also the gelling time is extremely slow (hours) and is dependent on the degradation of GDL. Moreover, the gelling may be performed over a wide range of pH, which is controllable using buffers.

In a further aspect of the invention there is provided a kit of parts comprising:
 i) a first solution, wherein the first polymer solution comprises a cross-linking agent and a first chelating agent,
 ii) a second solution, wherein the second solution comprises a displacing agent;
 wherein at least one of the first or second solutions contains an ionotropic polymer; and wherein:
  (iii) the ionotropic polymer has a lower affinity for the cross-linking agent than the first chelating agent, and
  (iv) the first chelating agent has a higher affinity for the displacing agent than the cross-linking agent.

The inventors have further found that cross-linked gels of the present invention can be achieved using reactants entirely in the liquid phase and under biocompatible conditions. The high cell compatibility of the cross-linked gels and individual components thereof are shown in FIGS. 4 and 5. Moreover, the process of the present invention can be modified to allow control over the time to gelation, from seconds to minutes, thereby making many new applications possible. Therefore, in an even further aspect of the invention there is provided a use of a cross-linked polymer gel according to the invention in manual printing, 3D printing or in the manufacture of large scale moldable gels.

Such printing compositions can contain dyes and/or pigments capable of colouring or functionally modifying such printed compositions. Such dyes or pigments are present in conventional quantities, for example 0.01-70 wt % of the final gelled composition, preferably 0.1-20 wt %, preferably 0.2-5 wt %. The dyes or pigments are preferably incorporated in the first solution and/or second solution according to the methods of the present invention. In a preferred embodiment, conductive inks are incorporated into the methods and compositions according to the present invention.

The cross-linked polymer gels of the present invention may also be used in magnetic resonance imaging. Use of paramagnetic metal ions, such as $Fe^{2+}$, $Mn^{2+}$, $VO^{2+}$ and $Ho^{3+}$ in the gelling preparation allows for contrast in magnetic resonance imaging, which lends this material to use in biomedical applications. Preferably this metal ion is the displacing agent that binds with the chelating agent, rendering the cross-linking agent free to bind the ionotropic polymer. Such paramagnetic metal ions are preferably present in quantities sufficient to provide adequate imaging, for example, in the range of 0.01-25 wt % of the final gelled composition, preferably 0.1-10 wt %, preferably 0.2-5 wt %. The paramagnetic metal ions may be only a portion of the displacing agent used in the method of the invention, i.e., the displacing agent may be a mixture of paramagnetic metal ions and non-paramagnetic metal ions.

Furthermore, the cross-linked polymer gel of the invention may be used in therapy. As used herein, the term therapy includes tissue regeneration, treatment or prevention of diseases such as diabetes mellitus type I, and heavy metal sequestration. In a further embodiment, there is provided a controlled release pharmaceutical formulation for use in therapy comprising the cross-linked polymer of the invention. Also provided is an oral formulation, injectable or wound dressing comprising the cross-linked polymer of the present invention. Other than the cross-liked gel and compositional by-products produced by the gelling method of the present invention, such pharmaceutical compositions contain conventional excipients for delivery via parenteral, oral or topical delivery.

In a further aspect of the invention, there is provided a cell or group of cells encapsulated within a cross-linked polymeric gel of the invention. Hydrogels of the present invention may be particularly useful for cell therapy. pH should be maintained in the acceptable ranges, known by the skilled person, for the specific cell or cells being encapsulated. For example, mammalian cells (e.g. human cells) typically reside in a near neutral pH of 7.4, and the optimal pH for tissue culture of mammalian cells is pH 7.2-7.4. Cells may survive adequately in the range of pH 6.6-7.8. Preferably one or more live cells are encapsulated in alginate.

In an even further aspect of the invention, the hydrogels may be used in microfluidic devices. Various microfluidic devices are known, some having co-flow regions for production of emulsions with two aqueous components. The gelling of hydrogels within small channels is a great challenge with current gelling methods, as it is difficult to obtain homogenous gels and at the same time avoid clogging of the micro channels due to premature gelation. Moreover, existing methods for gelation rely on cross-linking methods that are detrimental to cells, for example CaEDTA and acetic acid.

In an embodiment of the invention, the ionic exchange gelling technique of the present invention can be utilized in a microfluidic device, preferably a co-flow microfluidic device, for the facile encapsulation of a variety of different cell types with high cell-viability and efficient device friendly gelling. The present invention offers excellent cell viability, with both ungelled and gelled solutions being cell compatible.

Cell encapsulation is preferably performed via a droplet microfluidic device—i.e. a controlled emulsification process where oil, preferably a perfluorinated oil, more preferably 3M™ Novec™ 7500 engineered fluid (HFE7500), is mixed with a surfactant, preferably a fluorosurfactant, more preferably a biocompatible fluorosurfactant is used to break up two alginate flows (containing the two chelates and cells) mixed in a co-flow region prior to forming precursor alginate emulsions stabilized by surfactants. The gelling preferably occurs within these emulsions after cells are encapsulated. This approach is robust and simple to operate, requiring only one additional aqueous flow in the microfluidic device in the case of a co-flow device, and inexpensive chelates to be added to the alginate phase.

Microfluidic devices, preferably co-flow microfluidic devices, can be made according to prior art methods and cell samples are introduced. Two streams of polymer solution, preferably alginate, enter the device and are combined prior to droplet production, preferably in equal volumes. Uniform droplets of a narrow size distribution between 10-100 μm, preferably 30-70 μm, more preferably 40-60 μm, even more preferably 50-55 μm are produced in the fluidic device. An example microfluidic device that can be used is shown in FIG. 6a. FIG. 6b shows the micrograph of the region of the device at which encapsulation of cells occur. FIGS. 6c, and 6d show final gel beads containing encapsulated mammalian cells produced by this method. Gelling of the alginate relies on the ligand exchange method of the present invention, which achieves cell friendly, pH independent and microfluidics-compatible cell encapsulation in micro-hydrogels of alginate and other ionotropic polymers. The produced cell-loaded gels are preferably homogenous and monodisperse and highly biocompatible as demonstrated by excellent cell viability and survival following encapsulation and rinsing for several different cell types.

To demonstrate this, the growth of the naturally fluorescent cyanobacteria *Synechocystis* sp. PCC 6803 and *Chlamydomonas reinhardtii* CC-4532 algae was monitored in microgels until the cells formed microcolonies and escaped the microgel confinements. The cell proliferation in pure medium coincides with that of the rate observed for our encapsulated cells. Using a standard live/dead staining assay after the collection and subsequent rinsing of the hydrogels, a high cell viability (up to 90%) of encapsulated mammalian pre-osteoblast cells was achieved. FIG. 7 shows micrographs of the cyanobacteria *Synechocystis* sp. PCC 6803 encapsulated in alginate hydrogel beads. After encapsulation the beads were stored in BG 11 medium in a falcon tube at 30° C. and under continuous illumination and with light agitation. For imaging, a droplet of medium containing beads was placed on a cover glass and a second cover glass was placed on top. Images of samples were taken 0 h, 24 h, 48 h, 72 h, 1 week and 2 weeks after encapsulation. The bacteria divide within the alginate structure. After two weeks the bacteria colonies are large enough to burst out of the beads and escape. All images are taken on a Leica SP5 confocal microscope with a 20× lens. Images are overlaid images of bright field and fluorescent images capturing the auto fluorescence of chlorophyll produced by the algae. Scale bars: 20 μm. FIG. 8 shows micrographs of the algae *Chlamydomonas reinhardtii* CC-4532 encapsulated in alginate beads. After encapsulation, the beads were kept in medium (TAP-TrisPO4 and TrisAcPO4 medium) in a falcon tube and stored at 18° C. under continuous illumination and with light agitation. For imaging a droplet of medium containing beads was placed on a cover glass and a second cover glass was placed on top. Images of samples were taken 0(a), 24(b), 48(c) and 72(d) hours after encapsulation. The algae divide within the alginate structure. After 72 h the algae colonies are large enough to escape the beads. All images are taken on a Leica SP5 confocal microscope with a 20× lens.

Images are overlaid images of bright field and fluorescent images capturing the auto fluorescence of chlorophyll produced by the algae. Scale bars: 20 μm In an embodiment of the invention, one or more additional polymers capable of crosslinking to form a hydrogel by means other than ionotropic gelation (i.e. by chemical or thermal crosslinking) are blended with the polymer preparation of the present invention. Such additional polymers are preferably water soluble. The one or more additional polymers may be added to either or both of the individual precursor solutions prior to the initiation of gelling. Preferably the one or more additional polymer is selected from the list of proteins, polypeptides, glycosaminoglycans, polysaccharides, polyols, polyethers, polyesters, polyphosphazenes, polyamides and polyacrylamides. Even more preferably the one or more additional polymer is selected from the list of polyacrylamide, polyethylene glycol (PEG), polyurethane, polyvinylpyrrolidone (PVP), hyaluronic acid, chitosan derivatives, polyacrylic acid (PAA), polyvinyl alcohol (PVA), collagen, gelatin, and various polysaccharides. The additional polymer(s) are dispersed within the gel preparation of this invention. Upon gelation by the competitive ligand exchange gelling technique of the present invention, the additional polymer(s) are templated within the formed gel, and can then be crosslinked by another means. This has particular utility for plotting and 3D printing of gels otherwise unsuited to this technique due to limitations in the crosslinking method.

Figure 9:
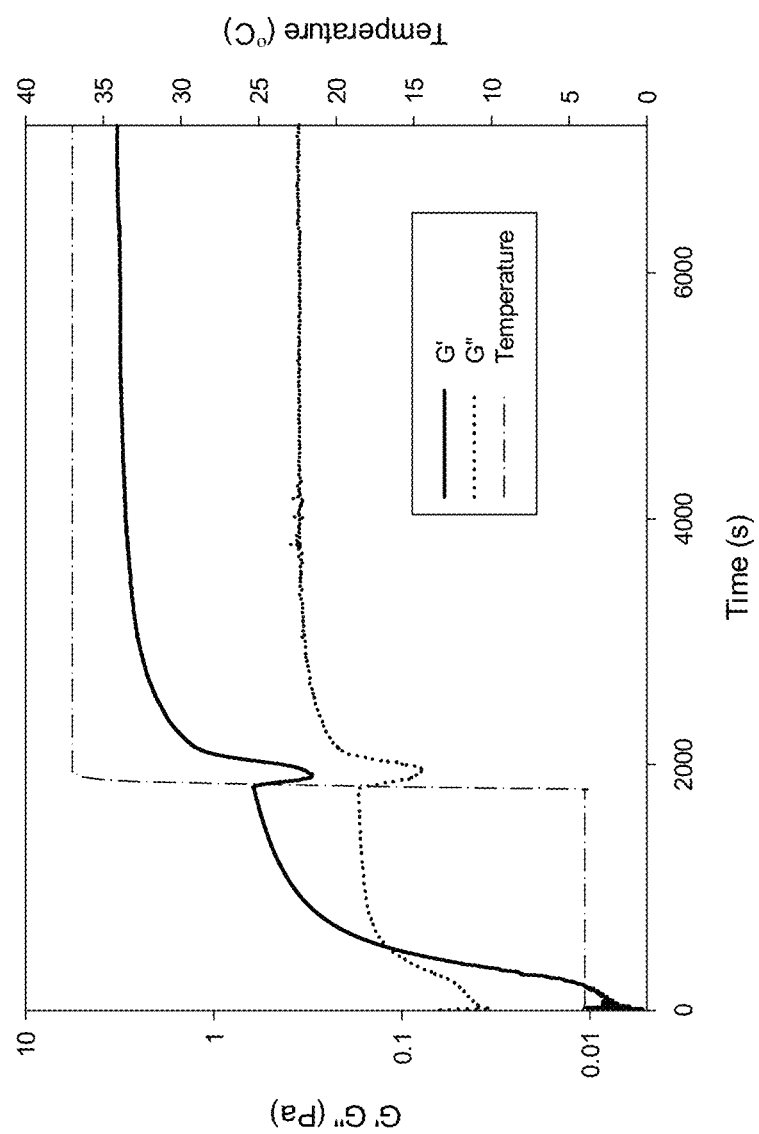

FIG. 9 shows rheological analysis of such a multiple polymer preparation. Here a dissolved collagen type I solution has been blended with alginate containing ions and chelates. Collagen dissolved in mild acid (e.g. acetic acid at ~pH 4) requires mild heating at 37° C. and near neutral pH to crosslink and form a hydrogel and does so within approximately 10-20 minutes, at 4° C. a pH neutral solution does not crosslink for several hours. The two alginate solutions both containing collagen but one containing a chelated crosslinking ion and the other containing a chelated displacing ion were mixed together at 4° C. in the rheometer. This temperature was held for 30 mins by which time the gel described by this invention had formed, as evidenced by a significant rise in the modulus of the sample. After 30 minutes, the temperature was rapidly (within 2 minutes) increased to 37° C., whereupon the collagen then crosslinked, as shown by a second rise in the modulus of the sample, following an initial reduction induced by the thermal effects. Such a preparation is useful to template a cell adhesive polymer such as collagen and this approach has been used to culture adherent cells in 3D as shown in FIG. 10.

EXAMPLES

Example 1

A CaEDTA/ZnEDDA, 1% Alginate hydrogel was prepared as follows:
Preparation of Alqinate-CaEDTA Solution:
 i) Alginate was dissolved to a concentration of 3 wt/vol % in water to produce an alginate stock;
 ii) An aqueous $CaCl_2$ solution was prepared having a concentration of 1M;
 iii) An aqueous EDTA solution was prepared using NaOH (0.5M, pH 8-9);
 iv) An aqueous buffer was prepared using MOPS (pH 7.0) at a concentration of 1M;

v) Next, the $Ca^{2+}$, EDTA and buffer solutions were mixed at a molar ratio of 1:1:1;
vi) pH was adjusted to pH 7.0;
vii) The alginate stock was mixed with CaEDTA-buffer solution in proportions to give 1% alginate concentration and 60 mM $Ca^{2+}$/EDTA/MOPS.

Preparation of Alqinate-ZnEDDA solution:
i) Alginate was dissolved to a concentration of 3 wt/vol % in water to produce an alginate stock;
ii) An aqueous solution of $Zn(CH_3CO_2)_2$ was prepared having a concentration of 1M;
iii) An aqueous solution of EDDA solution was prepared at using NaOH (0.5M pH 8-9);
iv) An aqueous buffer was prepared. MOPS was used (pH 7.0) at a concentration of 1M;
v) $Zn^{2+}$, EDDA and buffer solutions were mixed at a molar ratio of 5:6:5;
vi) pH was adjusted to 7.0;
vii) The alginate stock was mixed with ZnEDDA-buffer solution in proportions to give 1% alginate concentration and 60 mM $Zn^{2+}$/72 mM EDDA/60 mM MOPS.

Preparation of Hydrogel

Equal proportions of alginate-CaEDTA and alginate-ZnEDDA were mixed together to produce the hydrogel.

Example 2

The cells may be compartmentalised as follows. Preferably, a low viscosity hydrofluoroether (such as 3M™ Novec™ 7500 engineered fluid (HFE7500) that offers high gas transport and avoids swelling of PDMS devices, was used as the continuous phase. A fluorosurfactant (in this case, 2% (v/v) Krytox®-PEG600 based fluorosurfactant) was added to the continuous phase to facilitate droplet breakup, stabilize emulsions and to avoid coalescence. Two dispersed phases were used: (1) 0.6% (wt) alginate containing 84 mM $Ca^{2+}$/84 mM EDTA/40 mM MOPS at pH 6.7 and (2) 0.6% (wt) alginate containing 84 mM $Zn^{2+}$/100 mM EDDA/40 mM MOPS at pH 6.7. The two aqueous phases meet in a co-flow region in the microfluidic channels prior to droplet break-up.

The flow rates were set to 200 µL/hr for the continuous phase and 50 µL/hr for both aqueous phases by controlled injection using plastic syringes mounted on syringe pumps from Harvard Apparatus (PHD ULTRA). The syringes used for the dispersed phases contained magnets and were continuously stirred to avoid sedimentation of cells. Cells may be present in both aqueous phases to increase the encapsulation efficiency.

Example 3

A CaEDTA/ZnEDDA, 0.4% Alginate, 1% Collagen Type I hydrogel was prepared as follows:
Preparation of Alqinate-CaEDTA-Collaqen solution:
i) Alginate was dissolved to a concentration of 3 wt/vol % in water to produce an alginate stock;
ii) An aqueous $CaCl_2$ solution was prepared having a concentration of 1 M;
iii) An aqueous EDTA solution was prepared using NaOH (0.5 M, pH 8-9);
iv) An aqueous buffer was prepared using MOPS (pH 7.0) at a concentration of 1 M;
v) Next, the $Ca^{2+}$, EDTA and buffer solutions were mixed at a molar ratio of 1.1:1;
vi) pH was adjusted to pH 7.4;
vii) The alginate stock was mixed with CaEDTA-buffer solution in proportions to give 0.6% alginate concentration and 36 mM $Ca^{2+}$/EDTA/MOPS.
viii) The Alginate-CaEDTA solution was chilled to 4° C.
ix) Next cold (4° C.) 3 wt/vol % Collagen Type I from Rat Tail dissolved in 20 mM acetic acid was added to the cold alginate-CaEDTA solution at a volume ratio of 1:2

Preparation of Alqinate-ZnEDDA-Collaqen solution:
i) Alginate was dissolved to a concentration of 3 wt/vol % in water to produce an alginate stock;
ii) An aqueous solution of $Zn(CH_3CO_2)_2$ was prepared having a concentration of 1M;
iii) An aqueous EDDA solution was prepared using NaOH (0.5 M, pH 8-9);
iv) An aqueous buffer was prepared using MOPS (pH 7.0) at a concentration of 1 M;
v) Next, the $Zn^{2+}$, EDDA and buffer solutions were mixed at a molar ratio of 1.1:1;
vi) pH was adjusted to pH 7.4;
vii) The alginate stock was mixed with ZnEDDA-buffer solution in proportions to give 0.6% alginate concentration and 36 mM $Zn^{2+}$/EDDA/MOPS.
viii) The Alginate-ZnEDDA solution was chilled to 4° C.
ix) Next cold (4° C.) 3 wt/vol % Collagen Type I from Rat Tail dissolved in 20 mM acetic acid was added to the cold alginate-ZnEDDA solution at a volume ratio of 1:2

Preparation of Alqinate-Collaqen Hydrogel

Equal proportions of Alginate-CaEDTA-Collagen and Alginate-ZnEDDA-Collagen were mixed together at 4° C. and warmed to 37° C. to produce the hydrogel.

The invention claimed is:
1. A cross-linked polymeric gel comprising an ionotropic polymer or a mixture of different ionotropic polymers; a crosslinking agent; a displacing agent; a first chelating agent and a second chelating agent; and water; wherein the ionotropic polymer or the mixture of different ionotropic polymers have been crosslinked by the crosslinking agent to form a cross-linked polymeric gel; and wherein the crosslinking agent and the displacing agent are different multivalent metal ions.

2. The cross-linked polymeric gel according to claim 1, wherein
the ionotropic polymer or a mixture of different ionotropic polymers has a lower affinity for the crosslinking agent than the first chelating agent; and
the first chelating agent has a higher affinity for the displacing agent than the crosslinking agent.

3. The cross-linked polymeric gel according to claim 1, wherein the cross-linked polymeric gel is a gel of a mixture of different ionotropic polymers.

4. The cross-linked polymeric gel according to claim 1, further comprising one or more additional polymer(s) that are capable of crosslinking to form a hydrogel by means other than ionotropic gelation.

5. The cross-linked polymeric gel according to claim 1, further comprising one or more additional polymer(s) that are capable of crosslinking to form a hydrogel by means other than ionotropic gelation,
wherein
the one or more additional polymer(s) is/are templated within the cross-linked polymeric gel and crosslinked by means other than ionotropic gelation; and
the ionotropic polymer or the mixture of different ionotropic polymers have been crosslinked by the crosslinking agent to form a cross-linked polymeric gel prior to crosslinking of the one or more additional polymer(s) that are capable of crosslinking to form a hydrogel by means other than ionotropic gelation.

6. The cross-linked polymeric gel according to claim 1, wherein the second chelating agent is capable of chelating the displacing agent; and wherein the ionotropic polymer or the mixture of different ionotropic polymers has a lower affinity for the displacing agent than the second chelating agent, and wherein the second chelating agent has a lower affinity for the crosslinking agent than the ionotropic polymer or the mixture of different ionotropic polymers.

7. The cross-linked polymeric gel according to claim 1, wherein the crosslinking agent and the displacing agent are independently selected from multivalent metal ions selected from the group consisting of $Ca^{2+}$, $Zn^{2+}$, $Fe^{2+}$, $Fe^{3+}$, $Al^{3+}$, $VO^{2+}$, $Cu^{2+}$, $Ba^{2+}$, $Sr^{2+}$, $Ho^{3+}$, $Mg^{2+}$, $Mn^{2+}$, $Zn^{2+}$, $Pb^{2+}$, $Co^{2+}$ and $Ni^{2+}$.

8. The cross-linked polymeric gel according to claim 1, wherein the crosslinking agent comprises $Ca^{2+}$.

9. The cross-linked polymeric gel according to claim 1, wherein the displacing agent comprises a multivalent ion selected from the group consisting of $Zn^{2+}$, $Fe^{2+}$ and $Mn^{2+}$.

10. The cross-linked polymeric gel according to claim 1, wherein the displacing agent comprises $Zn^{2+}$.

11. The cross-linked polymeric gel according to claim 1, wherein the first chelating agent is selected from the group consisting of ethylenediamine-N,N'-disuccinic acid (EDDS), ethylenediamineietraacetic acid (EDTA), ethylenediamine-N.N'-diacetic acid (EDDA), propylenediamine-N,N,N',N'-tetraacetic acid (PDTA), 1,2-cyclohexanedinitrilotetraacetic acid (CDTA), ethylene glycol tetraacetic acid (EGTA), 1,2-bis(o-aminophenoxy)ethane-N,N,N',N'-tetraacetic acid (BAPTA), hydroxyphenyl-ethylenediamine (HPED), nitrilotriacetic acid (NTA), 2-[(2-Hydroxy-1, 1-bis (hydroxymethyl)ethyl)amino]ethanesulfonic acid, N-[Tris (hydroxymethyl)methyl]-2-aminoethanesulfonic acid (TES), 2-amino-2-(hydroxymethyl)-1,3-propanediol (TRIS), N-[Tris(hydroxymethyl)methyl]glycine (Tricine), porphyrin, citrate, phosphonates, amino acids, peptides and siderophores, preferably ethylenediamine-N,N'-disuccinic acid (EDDS), ethylenediaminetetraacetic acid (EDTA), ethylenediamine-N,N'-diacetic acid (EDDA, propylenediamine-N,N,N',N'-tetraacetic acid (PDTA), 1,2-cyclohexanedinitrilotetraacetic acid (CDTA) and aminoacetic acid (glycine).

12. The cross-linked polymeric gel according to claim 6, wherein the second chelating agent is selected from the group consisting of ethylenediamine-N,N'-disuccinic acid (EDDS), ethylenediamineietraacetic acid (EDTA), ethylenediamine-N.N'-diacetic acid (EDDA), propylenediamine-N,N,N',N'-tetraacetic acid (PDTA), 1,2-cyclohexanedinitrilotetraacetic acid (CDTA), ethylene glycol tetraacetic acid (EGTA), 1,2-bis(o-aminophenoxy)ethane-N,N,N',N'-tetraacetic acid (BAPTA), hydroxyphenyl-ethylenediamine (HPED), nitrilotriacetic acid (NTA), 2-[(2-Hydroxy-1, 1-bis (hydroxymethyl)ethyl)amino]ethanesulfonic acid, N-[Tris (hydroxymethyl)methyl]-2-aminoethanesulfonic acid (TES), 2-amino-2-(hydroxymethyl)-1,3-propanediol (TRIS), N-[Tris(hydroxymethyl)methyl]glycine (Tricine), porphyrin, citrate, phosphonates, amino acids, peptides and siderophores, preferably ethylenediamine-N,N'-disuccinic acid (EDDS), ethylenediaminetetraacetic acid (EDTA), ethylenediamine-N,N'-diacetic acid (EDDA, propylenediamine-N,N,N',N'-tetraacetic acid (PDTA), 1,2-cyclohexanedinitrilotetraacetic acid (CDTA) and aminoacetic acid (glycine).

13. The cross-linked polymeric gel according to claim 1, wherein the ionotropic polymer is selected from the group consisting of alginate, pectin, poly(galacturonate), carrageenan, dextran (and derivatives), gellan, scleroglucan, chitosan (and derivatives), water soluble polyphosphazenes, such as poly(bis(4-carboxyphenoxy)phosphazene), sodium polyacrylates, and polyamino acids.

14. The cross-linked polymeric gel according to claim 1, wherein the mixture of different ionotropic polymers is a mixture of one or more of the ionotropic polymers selected from the group consisting of alginate, pectin, poly(galacturonate), carrageenan, dextran (and derivatives), gellan, scleroglucan, chitosan (and derivatives), water soluble polyphosphazenes, such as poly(bis(4-carboxyphenoxy)phosphazene), sodium polyacrylates, and polyamino acids.

15. The cross-linked polymeric gel according to claim 1, wherein
the second chelating agent is capable of chelating the displacing agent;
the ionotropic polymer or the mixture of different ionotropic polymers has a lower affinity for the displacing agent than the second chelating agent;
the second chelating agent has a lower affinity for the crosslinking agent than the ionotropic polymer or the mixture of different ionotropic polymers;
the ionotropic polymer or a mixture of different ionotropic polymers has a lower affinity for the crosslinking agent than the first chelating agent;
the first chelating agent has a higher affinity for the displacing agent than the crosslinking agent; and
the cross-linked polymeric gel components have any one of the following combinations:

| | Ionotropic polymer | Cross-linking agent | First chelating agent | Displacing agent | Second chelating agent |
|---|---|---|---|---|---|
| 1 | Alginate | $Ca^{2+}$ | EDTA | $Zn^{2+}$ | EDDA |
| 2 | Alginate | $Ca^{2+}$ | EDTA | $Mn^{2+}$ | EDDA |
| 3 | Alginate | $Ca^{2+}$ | EDTA | $Fe^{2+}$ | EDDA |
| 4 | Alginate | $Ca^{2+}$ | CDTA | $Zn^{2+}$ | EDDA |
| 5 | Alginate | $Ca^{2+}$ | PDTA | $Zn^{2+}$ | EDDA |
| 6 | Alginate | $Ca^{2+}$ | CDTA | $Zn^{2+}$ | EDDS |
| 7 | Alginate | $Ca^{2+}$ | PDTA | $Zn^{2+}$ | EDDS |
| 8 | Alginate | $Ca^{2+}$ | EDTA | $Zn^{2+}$ | Glycine |
| 9 | Alginate | $Ca^{2+}$ | EDDS | $Zn^{2+}$ | Glycine |
| 10 | Pectin | $Ca^{2+}$ | PDTA | $Zn^{2+}$ | EDDA |
| 11 | Pectin | $Ca^{2+}$ | CDTA | $Zn^{2+}$ | EDDA |
| 12 | Pectin | $Ca^{2+}$ | PDTA | $Mn^{2+}$ | EDDS |
| 13 | Pectin | $Ca^{2+}$ | CDTA | $Mn^{2+}$ | EDDS |
| 14 | Pectin | $Ca^{2+}$ | EDTA | $Zn^{2+}$ | EDDA |
| 15 | Pectin | $Ca^{2+}$ | EDTA | $Zn^{2+}$ | EDDS |
| 16 | Poly(galacturonate) | $Ca^{2+}$ | PDTA | $Zn^{2+}$ | EDDA |
| 17 | Poly(galacturonate) | $Ca^{2+}$ | CDTA | $Zn^{2+}$ | EDDA |
| 18 | Poly(galacturonate) | $Ca^{2+}$ | PDTA | $Mn^{2+}$ | EDDS |
| 19 | Poly(galacturonate). | $Ca^{2+}$ | CDTA | $Mn^{2+}$ | EDDS |

16. A controlled release pharmaceutical formulation for use in therapy comprising the cross-linked polymeric gel of claim 1.

17. An oral formulation, injectable or wound dressing comprising the cross-linked polymeric gel of claim 1.

18. A cell or group of cells encapsulated within the cross-linked polymeric gel of claim 1.

19. A 3D-printed object comprising the cross-linked polymeric gel of claim 1.

20. A method of performing 3D printing comprising printing an object, the object comprising the cross-linked polymeric gel of claim 1.

21. A method for performing a magnetic resonance imaging of a subject, the method comprising administering a solution containing the cross-linked polymeric gel according to claim 1.

\* \* \* \* \*